United States Patent
Kwok et al.

(10) Patent No.: US 7,652,136 B2
(45) Date of Patent: Jan. 26, 2010

(54) DIARYLAMINOFLUORENE-BASED ORGANOMETALLIC PHOSPHORS AND ORGANIC LIGHT-EMITTING DEVICES MADE WITH SUCH COMPOUNDS

(75) Inventors: Hoi-Sing Kwok, Kowloon (HK); Wai-Yeung Wong, New Territories (HK); Xiao-Ming Yu, Kowloon (HK); Gui-Jiang Zhou, Kowloon (HK)

(73) Assignees: The Hong Kong University of Science and Technology, Kowloon, Hong Kong (CN); Hong Kong Baptist University, Kowloon, Hong Kong (CN)

( * ) Notice: Subject to any disclaimer, the term of this patent is extended or adjusted under 35 U.S.C. 154(b) by 141 days.

(21) Appl. No.: 11/520,148

(22) Filed: Sep. 12, 2006

(65) Prior Publication Data
US 2008/0091021 A1  Apr. 17, 2008

Related U.S. Application Data

(60) Provisional application No. 60/736,356, filed on Nov. 15, 2005.

(51) Int. Cl.
*C07F 15/00* (2006.01)
*H05B 33/14* (2006.01)

(52) U.S. Cl. .................. 546/10; 428/690; 428/917; 257/98; 546/2

(58) Field of Classification Search ............. 546/10, 546/2; 428/690, 917; 257/98
See application file for complete search history.

(56) References Cited

U.S. PATENT DOCUMENTS 6,670,645 B2 * 12/2003 Grushin et al. ............. 257/98

OTHER PUBLICATIONS

Adachi et al., "Nearly 100% Internal Phosphorescence Efficiency in an Organic Light Emitting Devices," *J. Appl. Phys.* Nov. 2001, 90(10), 5048-5051.
Adachi et al., "Highly-Efficiency Red Electrophosphorescent Devices," *Appl. Phys. Lett.* Mar. 2001, 78(11), 1622-1624.
Adamovich et al., "Highly Efficiency Single Dopant White Electrophosphorescent Light Emitting Diodes," *New. J. Chem.* 2002, 26, 1171-1178.
Baldo et al., "Phosphorescent Materials for Application to Organic Light Emitting Devices," *Pure Appl. Chem.* 1999, 71(11), 2095-2106.
Baldo et al., "Highly Efficient Phosphorescent Emission from Organic Electroluminescent Devices," *Nature.* Sep. 1998, 395, 151-153.
D'Andrade et al., "Efficient Organic Electrophosphorescent White-Light-Emitting Device with a Triple Doped Emissive Layer," *Adv. Mater.* Apr. 2004, 16(7), 624-628.
Duan et al., "New Iridium Complexes as Highly Efficient Orange-Red Emitters in Organic Light-Emitting Diodes," Adv. Mater. Feb. 2003, 15(3), 224-229.

D'Andrade et al., "Controlling Exciton Diffusion in Multilayer White Phosphorescent Organic Light Emitting Devices," *Adv. Mater.* Jan. 2002, 14(2), 147-151.
Furuta et al., "Platinum-Functionalized Random Copolymers for Use in Solution-Processible Efficient, Near-White Organic Light-Emitting Diodes," J. Am. Chem. Soc. 2004, 126(47), 15388-15389.
Gong et al., "Electrophosphorescence from a Polymer Guest-Host System with an Iridium Complex as Guest: Förster Energy Transfer and Charge Trapping," *Adv. Funct. Mater.* Jun. 2003, 13(6), 439-444.
Huang et al., "Highly Phosphorescent Bis-Cyclometalated Iridium Complexes Containing Benzoimidazole-Based Ligands," *Chem. Mater.* 2002, 16(12), 2480-2488.
Kavitha et al., "In Search of High-Performance Platinum Phosphorescent Materials for the Fabrication of Red Electroluminescent Devices," *Adv. Funct. Mater.* Feb. 2005, 15(2), 223-229.
Kwong et al., "High Operational Stability of Electrophosphorescent Devices," *Appl. Phys. Lett.* Jul. 2002, 81(1), 162-164.
Lamansky et al., "Highly Phosphorescent Bis-Cyclometalated Iridium Complexes: Synthesis, Photophysical Characterization, and Use in Organic Light Emitting Diodes," *J. Am. Chem. Soc.* 2001, 123(18), 4304-4312.
Lamansky et al., "Synthesis and Characterization of Phosphorescent Cyclometalated Iridium Complexes," *Inorg. Chem.* Mar. 2001, 40(7), 1704-1711.

(Continued)

*Primary Examiner*—Charnjit S Aulakh
(74) *Attorney, Agent, or Firm*—Robert D. Katz, Esq.; Cooper & Dunham LLP

(57) ABSTRACT

The present invention provides a diarylaminofluorene chromophore compound having the following structure:

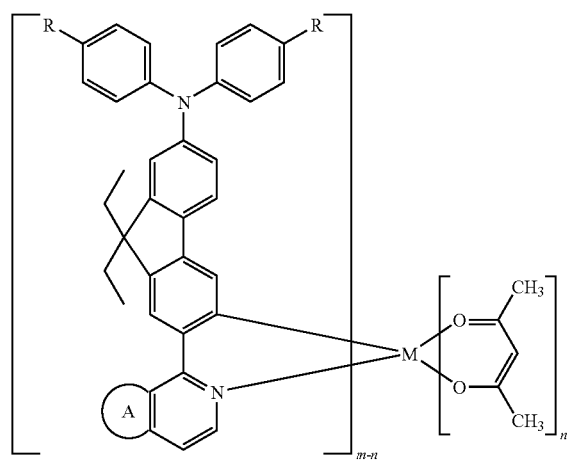

wherein:
M is a metal atom of Ir, Pt;
R is H, CH3, OCH3, or F;
A is none or six-member carbocyclic aromatic ring system;
$0 \geq m \geq 3$
$0 \geq n \geq 1$.

The invention also provides high-efficiency organic light-emitting devices fabricated using these compounds.

19 Claims, 11 Drawing Sheets

OTHER PUBLICATIONS

Markham et al., "Highly-Efficiency Green Phosphorescence from Spin-coated Single-Layer Dendrimer Light-Emitting Diodes," *Appl. Phys. Lett.* Apr. 2002, 80(15), 2645-2647.

Nazeerudin et al., "Highly Phosphorescence Iridium Complexes and Their Application in Organic Light-Emitting Devices," *J. Am. Chem. Soc.* 2003, 125(29), 8790-8797.

Okada et al., "Substituent Effects of Iridium Complexes for Highly Efficient Red OLEDs," *Dalton Trans.* 2005, 1583-1590.

Rayabarapu et al., "New Iridium Complexes with Cyclometalated Alkenylquinoline Ligands as Highly Efficient Saturated Red-Light Emitters for Organic Light-Emitting Diodes," *Adv. Mater.* Jun. 2005, 17(3), 349-353.

Su et al., "Highly Efficient Red Electrophosphorescent Devices Based on Iridium Isoquinoline Complexes: Remarkable External Quantum Efficiency Over a Wide Range of Current," *Adv. Mater.* Jun. 2003, 15(11), 884-888.

Tsuzuki et al., "Color Tunable Organic Light-Emitting Diodes Using Pentafluorophenyl-Substituted Iridium Complexes," *Adv. Mater,* Sep. 2003, 15(17), 1455-1458.

Tsutsui et al., "High Quantum Efficiency in Organic-Emitting Devices with Iridium-Complex as a Triplet Emissive Center," *Jpn. J. Appl. Phys.* Dec. 1999, 38(12B), L1502-L1504.

Wong, R.C., "High Operational Stability of Electrophosphorescent Devices" *Appl. Pys. Lett.* 2002, 81(1):162-64.

Wong, W.Y. et al., "Metallated Molecular Materials of Fluorene Derivatives and their Analogues," *Coord Chem. Rev.* 2005, 249, 971-997.

Wong, W.Y. et al., "Armophous Diphenylaminofluorene-Functionalized Iridium Complexes for High-Efficiency Electrophosphorescent Light-Emitting Diodes," *Adv. Funct. Mater.* 2006, 838-846.

Wong, W.Y. et al., "Efficient Organic Light-Emitting Diodes Based on Sublimable Charged iridum Phosphorescent Emitters," *Adv. Funct. Mater.* 2007, 315-323.

Wu et al., "Tuning the Emission and Morphology of Cyclometalated Iridium Complexes and Their Applications to Org. Light-Emitting Diodes," *J. Mater. Chem.* 2005, 15, 1035-1042.

Xie et al., "Reduction of Self-Quenching Effect in Organic Electrophosphorescence Emitting Devices via the Use of Sterically Hindered Spacers in Phosphorescence Molecules," *Adv. Mater.* Aug. 2001, 13(16), 1245-1248.

Yu, X.M. et al. "High-Efficiency White Organic Light-Emitting Devies Based on a Highly Amorphous Iridum (III) Orange Phosphor," *Chem. Mater.* 2006, 5097-5103.

Zhou, G.J. et al. "New Platinum (II) Complexes as triplet Emitters for High-Efficiency Monochromatic Pure Orange Electroluminescent Devices," *J. Org. Met. Chem.* 2007, 3461-3473.

\* cited by examiner

R = H; Ligand $L_1$

R = Me; Ligand $L_2$

R = OMe; Ligand $L_3$

R = F; Ligand $L_4$

R = H; Ligand $L_5$

R = Me; Ligand $L_6$

R = OMe; Ligand $L_7$

R = F; Ligand $L_8$

ITO: Indium-tin-oxide;

NPB: 4,4'-Bis[N-(1-naphthyl)-N-phenylamino]biphenyl;

CBP: N,N'-Dicarbazolyl-4,4'-biphenyl;

mCP: N,N'-Dicarbazolyl-3,5-benzene;

TPBI: 2,2',2"-(1,3,5-Phenylene)tris(1-phenyl-1H-benzimidazole)

DIARYLAMINOFLUORENE-BASED ORGANOMETALLIC PHOSPHORS AND ORGANIC LIGHT-EMITTING DEVICES MADE WITH SUCH COMPOUNDS

CROSS REFERENCE TO RELATED APPLICATION

This application claims the benefit of U.S. Provisional Application No. 60/736,356, filed Nov. 15, 2005.

FIELD OF THE INVENTION

This invention relates to electrophosphorescent complexes of iridium(III) and platinum(II) with diarylaminofluorene chromophores. It is also directed to organic light-emitting devices in which the active layer comprises such electrophosphorescent Ir(III) and Pt(II) complexes.

BACKGROUND OF THE INVENTION

There is a tremendous and growing interest in the research of organic-based optoelectronic materials for organic light-emitting diodes (OLEDs) which are promising elements for the next generation of flat-panel displays. Owing to its thin-film, light-weight, fast-response, wide-viewing-angle, high-contrast, and low-power attributes, OLED promises to be one of the major flat-panel-display technologies that can compete with the now-dominant liquid-crystal displays (LCDs) in the new millennium. Phosphorescent metal complexes that can be incorporated into OLEDs are under active investigation in academic and industrial R&D laboratories. This interest arises from the potential to increase device efficiency, relative to devices containing all-organic emissive materials, which is usually limited to an external quantum efficiency of around 5% based on singlet-state fluorescent materials. Phosphorescent emitters with heavy metal ions allow for circumvention of this limitation if the excitons generated by hole-electron recombination reside at a site where efficient spin-orbit coupling leads to strong singlet-triplet state mixing. Since both electrogenerated singlet and triplet excitons can be harvested for light emission in these complexes, the internal quantum efficiency of phosphorescent emitters can approach 100% theoretically (Adachi et al., J. Appl. Phys. 2001, 90, 5048).

While this research field has many interesting and novel opportunities on account of its huge market share in next generation flat-panel display technologies, it is now identified that molecules or polymers with specific functions such as hole transportation, electron transportation, emission and thermal stability are ideal for this purpose. Current focus and challenge for OLEDs lie in the optimization of EL cell structures and the use of electrophosphorescence for the improvement of device performance. The latter work has relied on the use of spin triplet states toward light emission (i.e. triplet-harvesting). Hole-electron recombination in OLEDs produces both singlet and triplet excitons within the molecular thin film. For most fluorescent compounds, only the singlet state is emissive, leading to a significant limitation in the OLED efficiency. An excellent method to efficiently harvest energy from the triplet states involves the incorporation of third row heavy metals and these metal complexes permit the opening of an additional radiative recombination channel because of the associated strong spin-orbit coupling, resulting in a harvesting of up to nearly 100% of the excited states to photon creation.

This line of research would set a new benchmark for the theoretical efficiency limit, namely 75% for triplet emission as opposed to the 25% for singlet emission. The scope and diversity of studies on metal-organic phosphors in the realm of materials science have continued to expand and the interest in these materials and their electrophosphorescent properties spans the entire globe. Over the years, significant advances were made in this area and there is a great potential to excel in the exploration of triplet emitters for organic molecular optoelectronics that can be developed for use in display technology.

Heavy metal compounds of iridium(III) and platinum(II) can be used as emissive traps or dopants in OLEDs, leading to unprecedented quantum efficiencies for these devices. Both the EL efficiency and the emission wavelength of these electrophosphor-doped devices are strongly influenced by the structural features of organic ligand chromophores which are generally 2-arylpyridine derivatives or other nitrogen-containing heterocycles (abbreviated as C^N). Although red-, green-, and blue-emitters with excellent color purity and sufficient luminous efficiency are required for full-color display applications, there is also a continuing demand for monochromatic emitters that afford a bright color, such as yellow, orange or light blue, for multiple-color display purposes.

On the other hand, white organic light-emitting diodes (WOLEDs) have drawn much recent attention in the scientific community because of their potential use in display backlights, full color applications, as well as in solid-state lighting purposes. WOLEDs make attractive candidates as future illumination sources over the conventional incandescent bulbs and fluorescent lamps for several reasons, including compact size, the suitability for fabrication on flexible substrates, low operating voltages, and good power efficiencies. In particular, WOLEDs employing phosphorescent materials have led to significant improvements in efficiency, targeting backlights for full color active-matrix displays combined with color filters. While electrophosphorescent OLEDs have been shown to have very high external quantum efficiency when used for monochromatic light emission, their incorporation into a white emitting device should similarly lead to high-efficiency WOLEDs.

The present work called for a highly topical area in the development of a novel series of heavy metal organometallic triplet emitters containing diarylaminofluorene components that can be used as efficient phosphorescent dopants in high-efficiency OLEDs applications. Fluorene-based chromophores hold great promise as highly stable and efficient emissive cores in the synthesis of useful metal complexes (Wong, Coord. Chem. Rev. 2005, 249, 971). Fluorene derivatives are attractive candidates for optoelectronic applications because of their good thermal and chemical stability, high emission quantum yields and the ease of functionalization of the fluorene at 2-, 7- and 9-positions. However, most of the related reports involving fluorene cores have been concentrated on polymer-based devices where the fluorene-containing phosphor is processed with a polymer host by the spin-coating method (Wu et al., J. Mater. Chem. 2005, 15, 1035 and Gong et al., Adv. Mater. 2003, 15, 45). It is also known that a large hole-injection barrier for organic fluorene-based molecules often limits their device efficiency. Since triphenylamine groups are known to possess a superior hole-transport mobility, and glass-forming aromatic amino derivatives, such as N,N'-diphenyl-N,N'-bis(3-methylphenyl)-[1,1'-biphenyl]-4,4'-diamine (TPD) and 4,4'-bis[N-(1-naphthyl)-N-phenylamino]biphenyl (NPB), are widely used for the preparation of hole-transporting materials used in OLEDs, we envision that triarylamines or their derivatives can be incorporated into the fluorene nucleus to improve the hole-injection/hole-transporting properties and morphological stability. The molecular design of amorphous organometallic phosphors capable of efficient visible emission in OLEDs is highly challenging and it is desirable to design new ligand systems for heavy metal complexes with good amorphous properties and improved functional properties. To our knowledge, there are no literature reports exploring arylamine-substituted fluorene-based electrophosphors for small-molecule OLEDs. The major impetus for the present invention is stimulated from the contention that the use of arylamino-fluorene ligand chromophores can improve the morphological stability and charge-transport properties of metalated phosphors.

Others have attempted to provide phosphorescent compounds and devices made from those compounds. U.S. Pat. No. 6,835,469 B2 (Kwong) discusses phosphorescent organometallic complexes comprising phenylquinolinato ligands, and high efficiency organic light emitting devices comprising these compounds.

U.S. Pat. No. 6,902,830 B2 (Thompson) provides organic light emitting devices wherein the emissive layer comprises a host material containing an emissive molecule. The emissive molecule is a phosphorescent organometallic complexes, including cyclometalated platinum, iridium and osmium complexes.

U.S. Pat. No. 6,573,651 B2 (Adachi) is directed to OLED structures comprising an anode layer, a hole injecting layer (HIL) in direct contact with the anode layer, an emissive organic electron transporting layer (ETL) in direct contact with the hole injecting layer, and a cathode layer in direct contact with the emissive organic electron transporting layer. The emissive organic electron transporting layer comprises an organic electron transporting material and an organic hole-trapping emissive material, for example, an organic phosphorescent material that produces emission from a triplet excited state of an organic molecule.

U.S. Pat. No. 6,670,645 B2 (Grushin) relates substituted 2-phenylpyridines, phenylpyrimidines, and phenylquinolines electroluminescent Ir(III) compounds and devices that are made with the Ir(III) compounds.

SUMMARY OF THE INVENTION

The invention provides a diarylaminofluorene chromophore compound having the following structure:

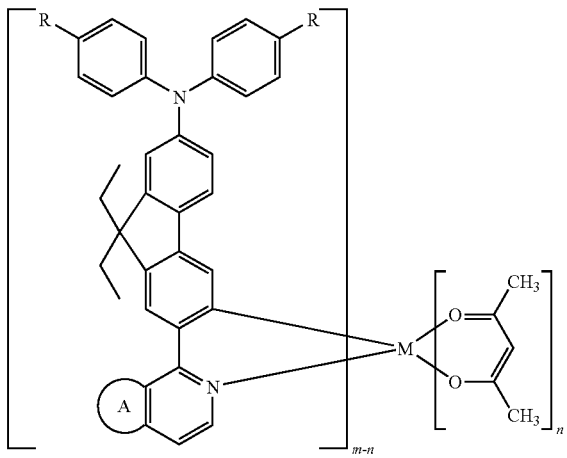

wherein:

M is a metal atom of Ir, Pt;

R is H or any substituent such as $CH_3$, $OCH_3$, F;

A is none or six-member aromatic ring system;

m is at least 1;

n is at least zero.

The invention also provides an organic light-emitting device, comprising an anode, a cathode and an emissive layer disposed between the anode and the cathode, wherein the emissive layer comprises an emissive material having the structures:

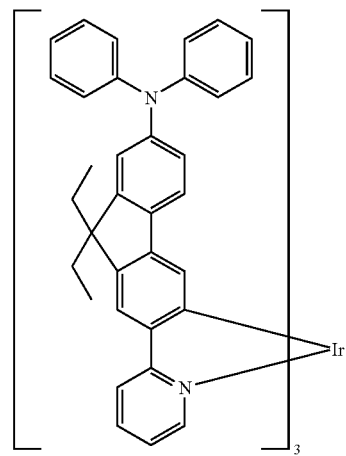

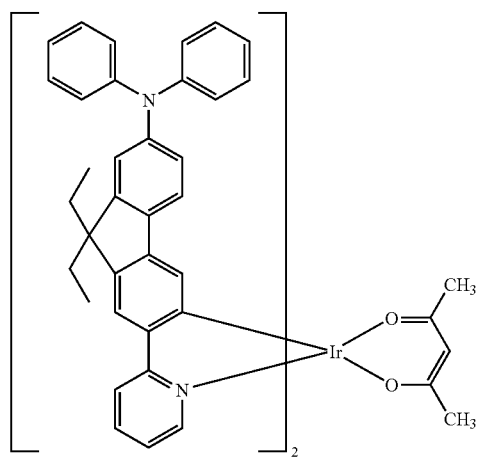

The invention further provides an organic light-emitting device, comprising an anode, a cathode, and an emissive layer disposed between the anode and the cathode, wherein the emissive layer comprises an emissive material having the structure:

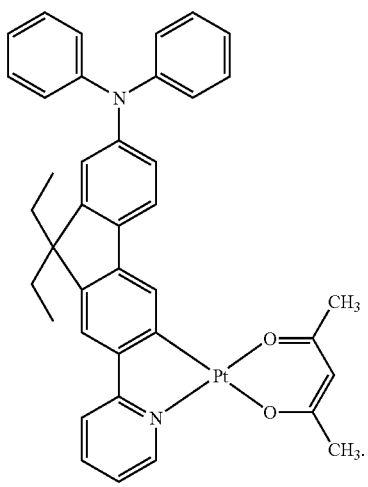

DETAILED DESCRIPTION OF PREFERRED EMBODIMENTS

The invention provides a class of organometallic phosphorescent materials containing diarylaminofluorene chromophores represented by the following formula:

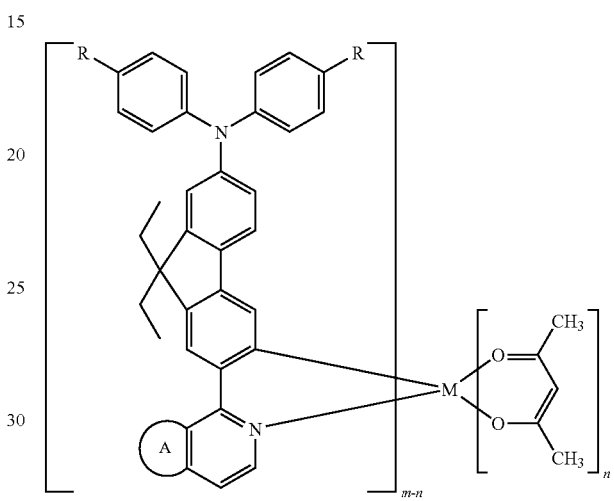

wherein:

M is a metal atom of Ir, Pt;

R is H or any substituent such as $CH_3$, $OCH_3$, F;

A is none or six-member aromatic ring system;

m is at least 1;

n is at least zero.

Figure 1:
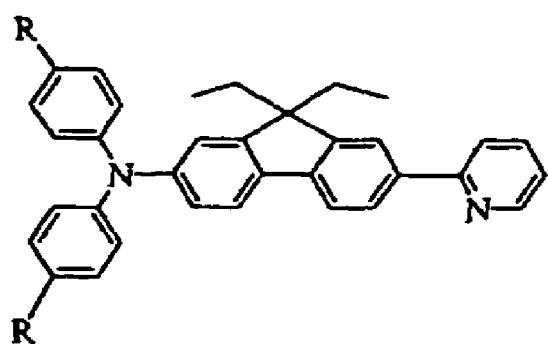
FIG. 1 shows the structures of ligands $L_1$-$L_8$.
Figure 1:
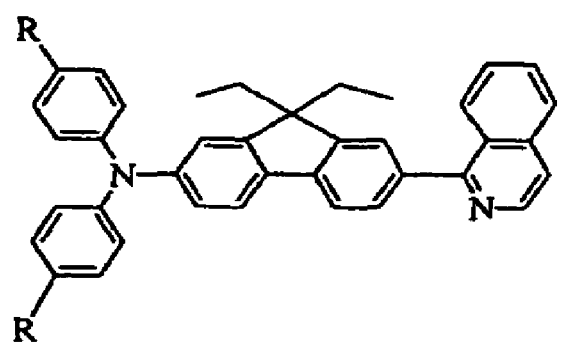
Figure 2:
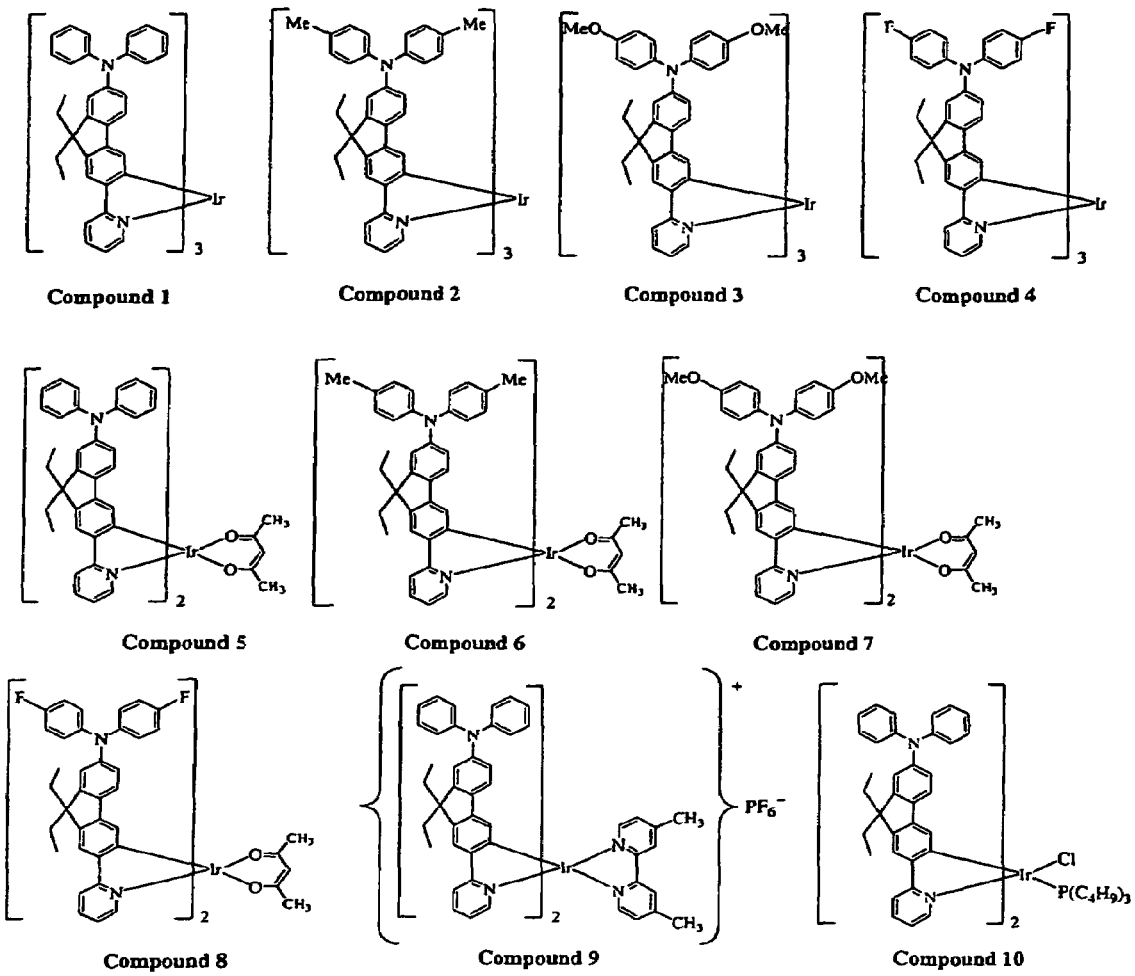
FIG. 2 shows the structures of compounds 1-10.
Figure 3:
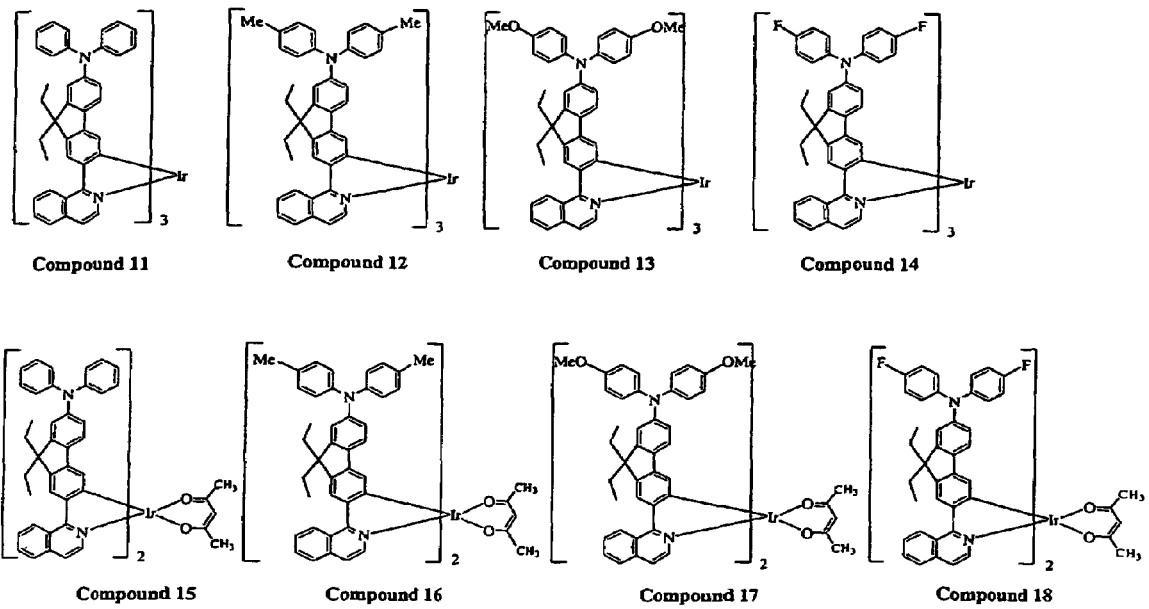
FIG. 3 shows the structures of compounds 11-18.
Figure 4:
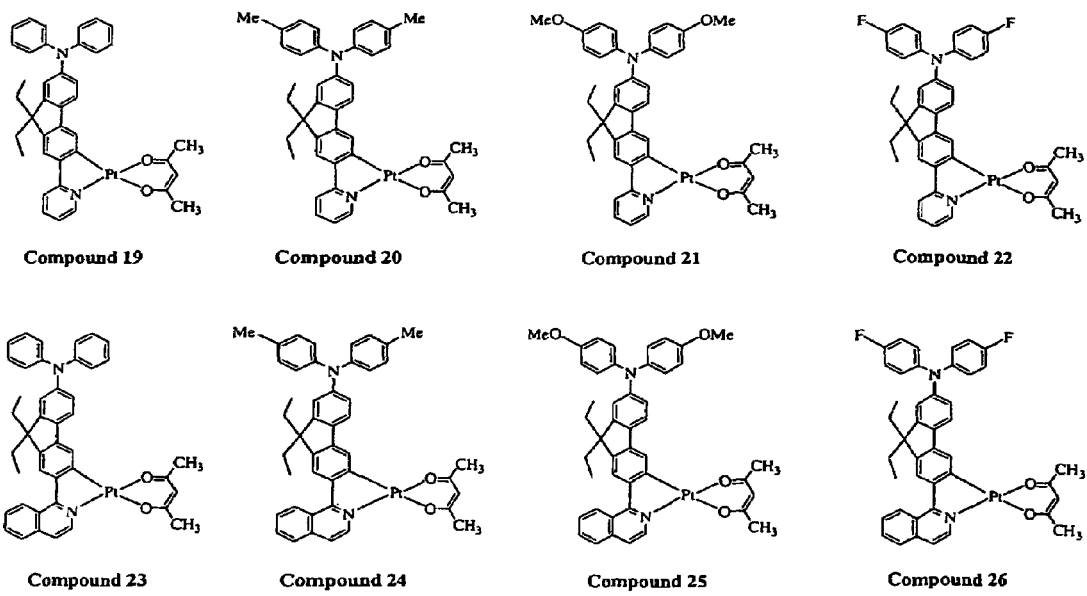
FIG. 4 shows the structures of compounds 19-26.
Figure 5:
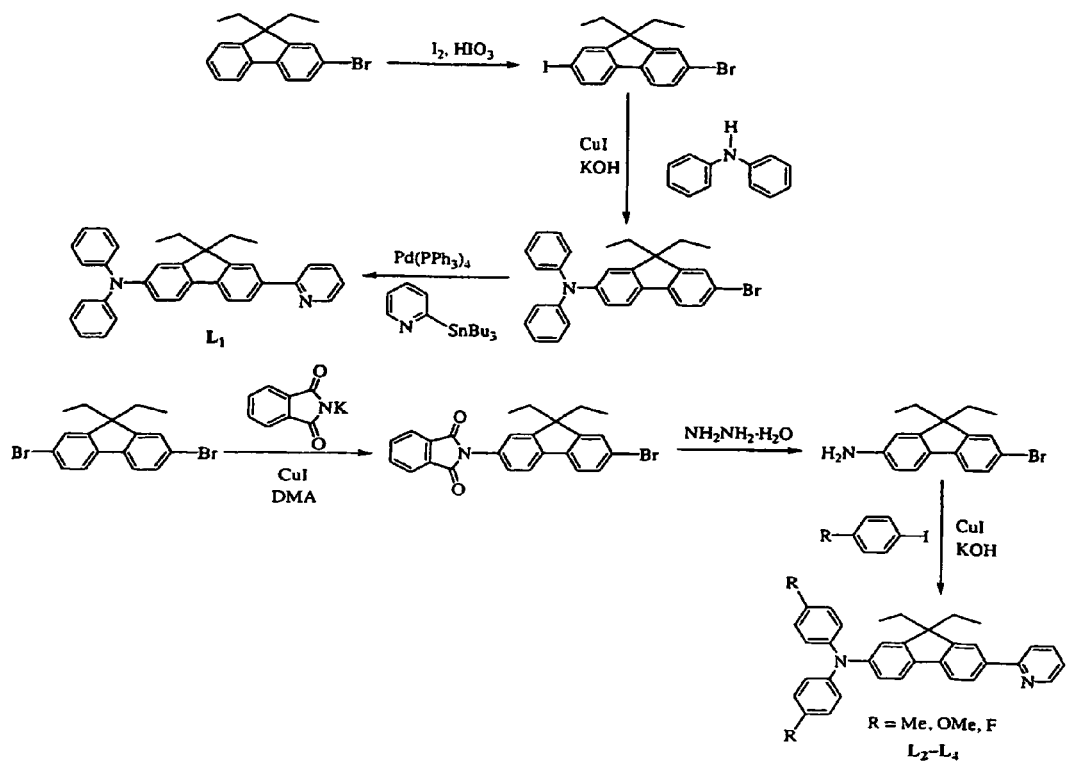
FIG. 5 shows a schematic diagram for preparing compounds $L_1$-$L_4$.
Figure 6:
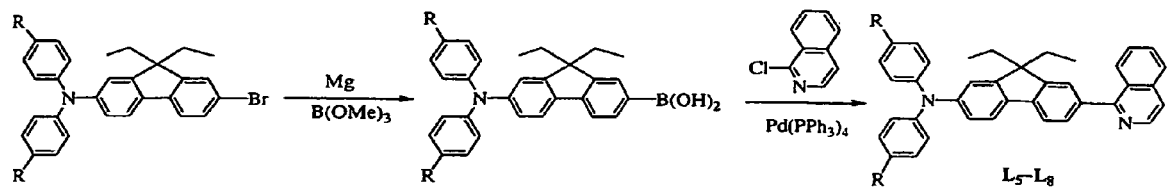
FIG. 6 shows a schematic diagram for preparing compounds $L_5$-$L_8$.
Figure 7:
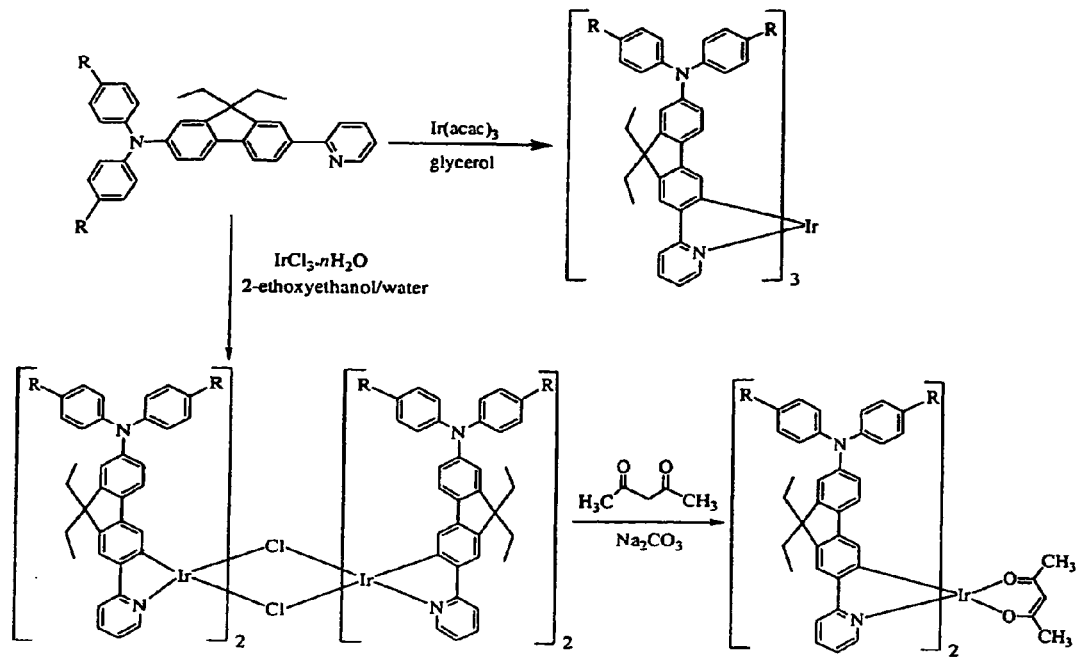
FIG. 7 shows a schematic diagram for preparing iridium (III) compounds 1-8.
Figure 8:
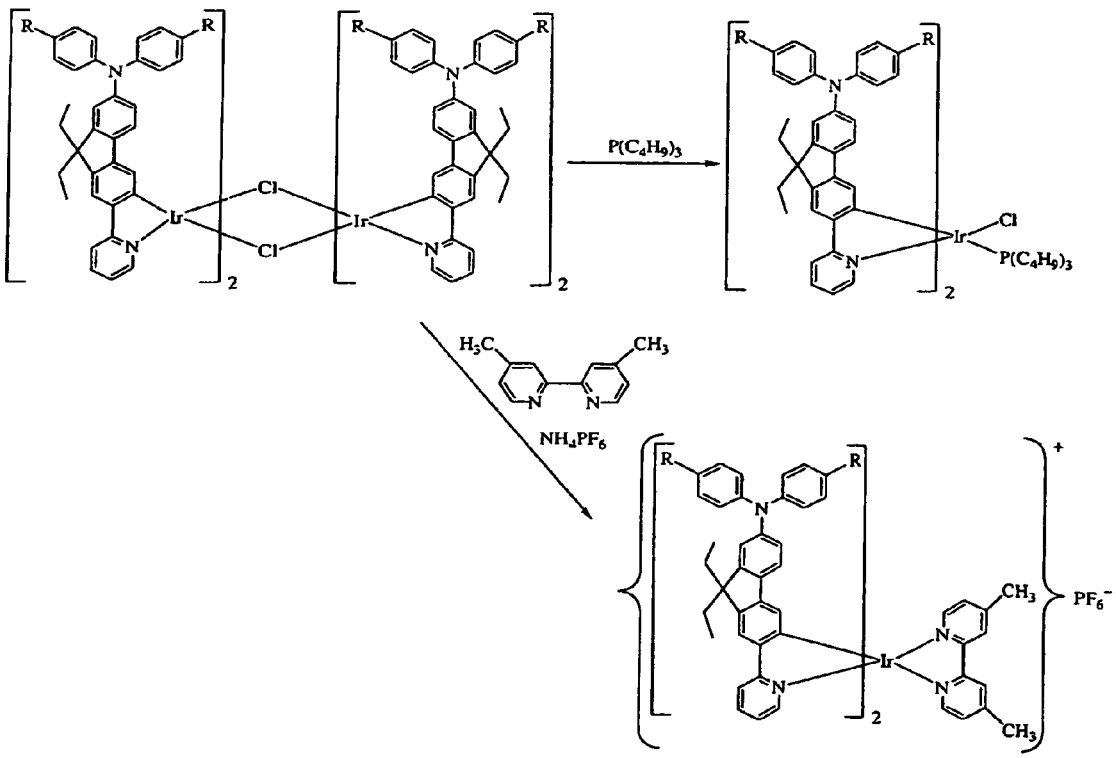
FIG. 8 shows a schematic diagram for preparing iridium (III) compounds 9 and 10.
Figure 9:
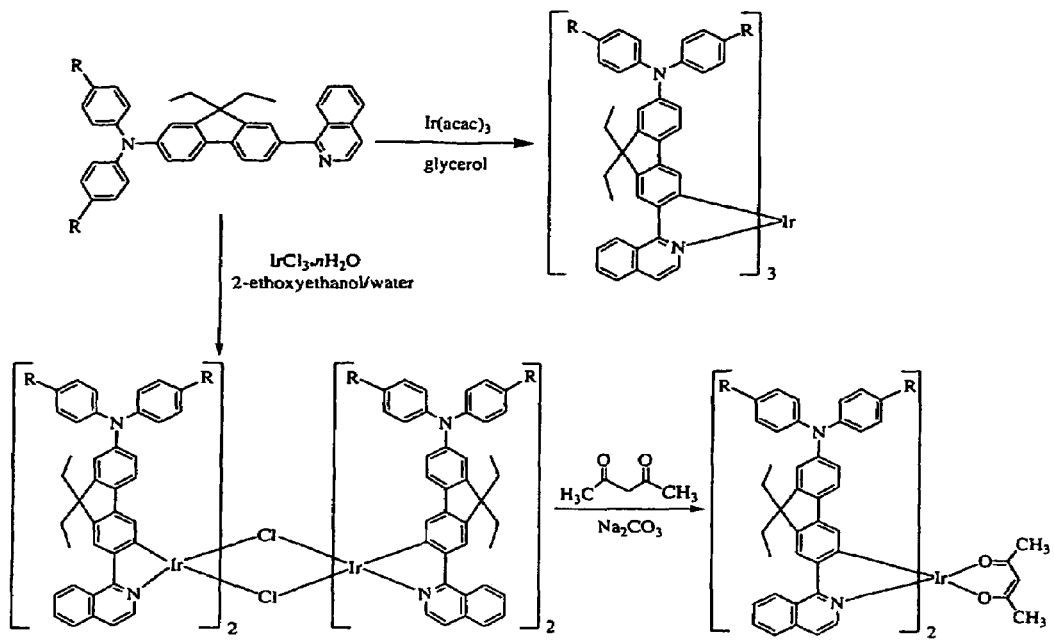
FIG. 9 shows a schematic diagram for preparing iridium (III) compounds 11-18.
Figure 10:
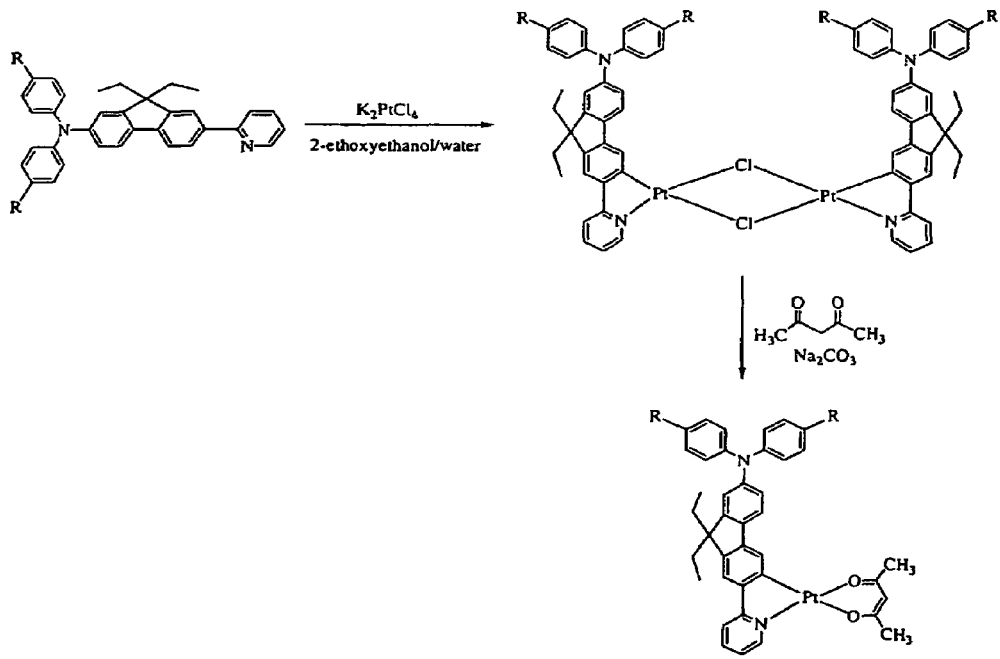
FIG. 10 shows a schematic diagram for preparing platinum (II) compounds 19-22.
Figure 11:
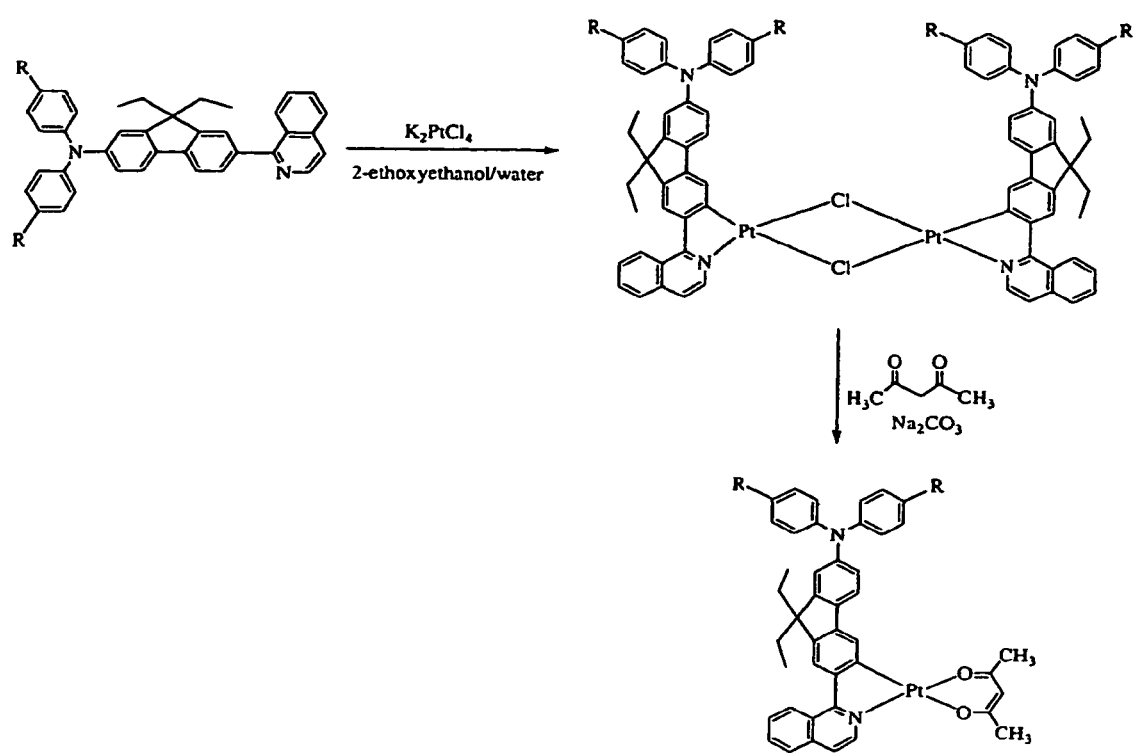
FIG. 11 shows a schematic diagram for preparing platinum (II) compounds 23-26.

The present invention provides methods for obtaining highly amorphous and phosphorescent organometallic complexes comprising diarylaminofluorene groups (Formula I-III). Novel bifunctional cyclometalated iridium and platinum complexes containing diarylaminofluorene unit are synthesized in which the hole-transporting and electroluminescent functional groups are integrated into one molecular unit (FIGS. 2-4). We found that the diarylamino moiety end-capped onto highly luminescent fluorene backbone can offer a good channel to lower the ionization potential, induce morphologically stable amorphous thin-film formation, and enhance the thermal stability of the complexes. These organometallic complexes show very high glass-transition temperatures. These metal phosphors emit a wide spectrum of colors at room temperature in both solution and the solid state. High-efficiency electrophosphorescent organic light-emitting devices can be fabricated using these complexes as phosphorescent dopant emitters.

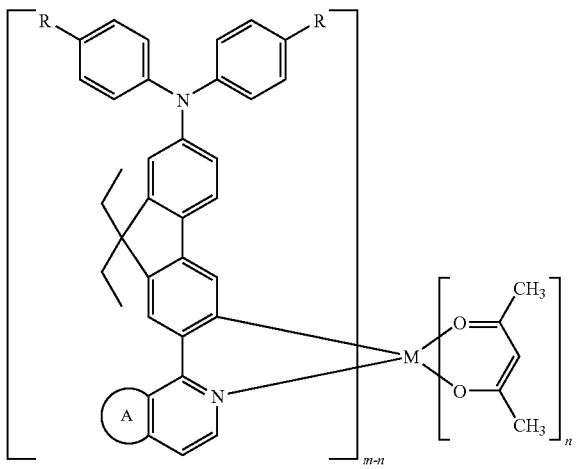

(I)

wherein:
M is a metal atom of Ir, Pt;
R is H or any substituent such as $CH_3$, $OCH_3$, F;
A is none or six-member aromatic ring system;
m is at least 1;
n is at least zero.

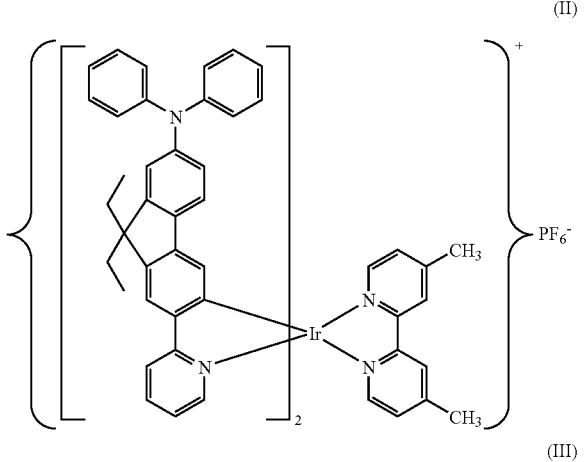

(II)

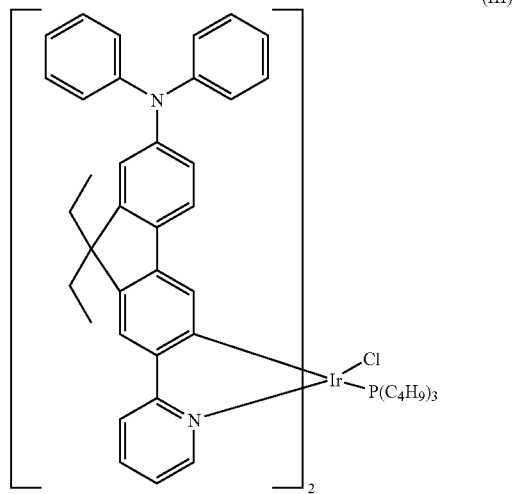

(III)

The approaches for preparing compounds described herein are embodied by the present invention. For the preparation of iridium-containing compounds, the metal halide complex can be $IrCl_3 \cdot nH_2O$ and $Ir(acac)_3$. These metal complexes are well known in the art and commercially available. FIGS. 5-11 show the synthetic protocols for the pyridyl- and isoquinolinato ligands $L_1$-$L_8$ and the new iridium(III) and platinum(III) complexes 1-24. The key compounds in our studies are the cyclometalating ligands $L_1$-$L_8$, which can be obtained from the Stille or Suzuki coupling reactions. Coupling procedures can be conducted in the presence of palladium(II) catalysts. The boronic acid and tributylstannyl starting materials can be obtained from commercial sources or synthesized by methods known in the art. For example, ligand L1 can be obtained from the Stille coupling of (7-bromo-9,9-diethylfluoren-2-yl) diphenylamine (Kannan et al., Chem. Mater. 2001, 3, 1896) with 2-(tributylstannyl)pyridine. 1-Chloroisoquinoline can react with (7-boronic acid-9,9-diethylfluoren-2-yl)diphenylamine to afford Ls (Okata et al., Dalton Trans. 2005, 1583). The design rationale of L1-Lg is that each of them possesses both the diarylamino moiety as the hole-transporting unit and the 2-phenylpyridine or 2-phenylisoquinoline group as a cyclometalating site. The homoleptic iridium (III) complexes are obtained by direct thermal reaction of $Ir(acac)_3$ with $L_1$-$L_8$ in refluxing glycerol. The heteroleptic iridium(III) compounds are synthesized in two steps from the cyclometalation of $IrCl_3 \cdot nH_2O$ with L1-Lg to form initially the chloride-bridged dimer $[Ir(C\hat{\ }N)_2Cl]_2$ followed by treatment with acetylacetone in the presence of $Na_2CO_3$. Cationic compound 9 can be made by cleavage of the iridium dimer made from $L_1$ with the diimine ligand followed by metathesis reaction with $NH_4 PF_6$. Reaction of the aforesaid iridium dimer with a tertiary phosphine readily affords the neutral complex 10. Platinum cyclometalated complexes can be synthesized by reaction of $K_2PtCl_4$ with L1-L8 followed by treatment with acetylacetone in the presence of a base such as $Na_2CO_3$. Purification of the reaction mixture by preparative thin-layer chromatography furnished the compounds as air-stable powders in high purity. All of the new compounds were fully characterized by NMR spectroscopy and FAB mass spectrometry and have well-defined structures. Syntheses of exemplary compounds of the present invention are provided in Examples 2-11.

The compounds of the present invention are photoluminescent (Table 1 below). In many embodiments, the present compounds are efficient phosphors at room temperature, having, for example, a significant portion of luminescence arising from phosphorescent emission. The compounds can emit at different colors, including red, orange and yellow. The color of emission can be estimated from the photoluminescence spectrum. According to some embodiments, compounds of the present invention can have a photoluminescence maximum at a wavelength from about 560 to about 660 nm. In fact, emission color can be deliberately controlled, or tuned in compounds of the present invention by judicious selection of substituents. Since emission color is sensitive to the energy gap between the highest occupied molecular orbital (HOMO) and lowest unoccupied molecular orbital (LUMO) energy levels of the compound, substituents that predictably affect either or both of these molecular orbitals can be purposefully incorporated into compounds of the present invention to achieve a certain color. As is evident, emission color can be deliberately red-shifted or blue-shifted upon selection of ligand and substitution site in order to obtain a desired hue. Accordingly, the present invention encompasses methods of tuning the emission wavelength. Example 12, infra, details results from some representative compounds of the invention.

optimize the device efficiency, concentration dependence experiment was carried out in a range between 1 and 12 wt.-%.

TABLE 1

| Absorption (293 K) | Emission (293 K) | | | | | | |
|---|---|---|---|---|---|---|---|
| $\lambda_{abs}$ [nm][a] $CH_2Cl_2$ | $\lambda_{em}$ [nm] $CH_2Cl_2$ | $\lambda_{em}$ [nm] Film | $\Phi_P$[b] | $\tau_P$ [µs][c] | $k_r$ [s$^{-1}$] | $k_{nr}$ [s$^{-1}$] | $\tau_P$ [µs][d] |
| 1  309 (4.86) | 555 | 567 | 0.12 | 0.08 | $1.5 \times 10^6$ | $1.1 \times 10^7$ | 0.08 |
|    375 (4.91) | 595 sh | 607 sh | | (0.67) | | | (0.55) |
|    415 (4.74) | | | | | | | |
|    478 sh (3.97) | | | | | | | |
| 5  297 (4.70) | 564 | 575 | 0.13 | 0.11 | $1.2 \times 10^6$ | $7.9 \times 10^6$ | 0.05 |
|    387 (4.70) | 607 sh | 622 sh | | (0.85) | | | (0.61) |
|    408 sh (4.68) | | | | | | | |
|    478 sh (3.84) | | | | | | | |

[a]logε values are shown in parentheses.
[b]Measured in degassed $CH_2Cl_2$ relative to fac-[Ir(ppy)$_3$] ($\Phi_P$ = 0.40), $\lambda_{ex}$ = 380 nm.
[c]In degassed $CH_2Cl_2$ at 293 K. The radiative lifetimes $\tau_r$ (µs) are shown in parentheses.
[d]For a solid film at 293 K. Numbers in parentheses were obtained at 77 K. sh = shoulder.

The decomposition temperatures of the metal phosphors were determined from thermogravimetric analysis (TGA) measured under nitrogen stream. The thermal stability data reveal that these metal complexes have excellent thermal stability with decomposition temperatures in excess of 400° C. for most of them, and they are found to sublime before their decomposition temperatures ($T_{dec}$). For instance, compounds 1 and 5 have $T_{dec}$ values of 473 and 432° C., respectively and are sufficiently stable with respect to sublimation for a fabrication process by the vacuum deposition method. Differential scanning calorimetry (DSC) data showed no crystallization and melting peaks but only glass-transition temperature ($T_g$). All of them showed a high $T_g$ value and exist as highly amorphous solids which are resistant to crystallization. Usually, an amorphous film with higher $T_g$ is desired for OLEDs of high stability and high efficiency. Our results suggest that the diarylamino moieties play a pivotal role in enhancing the amorphous nature of the phosphor molecules, leading to materials of high $T_g$ values. This would give rise to new complexes with improved compatibility between the phosphorescent dopant and the organic host and eventually lead to highly efficient electrophosphorescent small-molecule OLEDs.

The present invention further includes organic light-emitting devices comprising a compound of Formula I, II, or III. These organometallic phosphors have very good film- and glass-forming properties for evaluating their electrophosphorescent ability. The electrophosphorescent OLEDs in the four-layer configuration of glass/ITO/NPB/dye:CBP/TBPI/LiF/Al were fabricated. N,N'-dicarbazole-4,4'-biphenyl (CBP) acts as a host material for the electrophosphor, NPB as a hole-transport layer, 2,2',2"-(1,3,5-phenylene)tris (1-phenyl-1H-benzimidazole) (TBPI) as both a hole-blocker and an electron-transporter, and LiF as an electron-injection layer. Here, TBPI, instead of the commonly used 2,9-dimethyl-4,7-diphenyl-1, 10-phenanthroline (BCP) or tris(8-hydroxyquinolinato) aluminum (Alq$_3$), was adopted for the devices to confine excitons within the emissive zone since it has a higher electron mobility and hole-blocking ability. We chose CBP as the host layer for device fabrication because of the excellent overlap of the UV-vis absorption of these complexes with the PL spectrum of CBP, and such guest-host systems meet the requirement for efficient Forster energy transfer from the CBP host singlet to the guest complexes. To The invention has been described in detail with certain preferred embodiments thereof (infra), but it will be understood the variations and modifications can be effected within the scope of the invention. The following examples are presented for a further understanding of the present invention.

Example 1

Compound and Device Properties

A series or organometallic complexes of iridium and platinum 1-26 based on diarylaminofluorene chromophores are synthesized, characterized, and used as emissive dopants in organic light-emitting devices having the device structure glass/ITO/NPB/CBP:dopant/TPBII/LiF/Al. Representative data for the photophysical and other properties of the compounds as well as for the devices are illustrated in Tables 1-3. In particular, new homoleptic and heteroleptic cyclometalated iridium complexes of L1-Lg are shown to be amorphous solids with high glass-transition temperatures. These metal-based phosphors show organic electrophosphorescence with very high efficiencies in different regions of the visible spectrum. The incorporation of electron donating diarylamino groups to the fluorene skeleton is found to increase the HOMO levels and add the hole-transporting ability to the phosphorescent center.

Example 2

Synthesis of Compound 1

Ir(acac)$_3$ (0.15 g, 0.30 mmol) and L$_1$ (0.50 g, 1.07 mmol) were mixed in glycerol (16 mL) under a N$_2$ atmosphere. The reaction mixture was heated to 220° C. for 18 h, after which time the mixture was cooled to room temperature and water (50 mL) was added. The resulting mixture was extracted with $CH_2Cl_2$ (3×100 mL) and the organic phase was dried over MgSO$_4$. Upon solvent removal under vacuum, the residue was purified by column chromatography using $CH_2Cl_2$ as eluent to afford the title compound as an orange solid (0.10 g, 21%). MS (FAB): m/z 1589 (M+). $^1$H NMR (CDCl$_3$): δ (ppm) 7.91 (d, J=8.1 Hz, 3H, Ar), 7.68 (d, J=54 Hz, 3H, Ar), 7.58-7.52 (m, 6H, Ar), 7.20-6.77 (m, 45H, Ar), 1.97-1.82 (m, 12H, Et), 0.45-0.32 (m, 18H, Et). $^{13}$C{$^1$H} NMR (CDCl$_3$): δ (ppm) 167.00, 160.89, 152.11, 148.11, 147.25, 146.35, 142.91, 142.42, 141.30, 135.15, 135.40, 128.96, 127.79, 123.96, 123.17, 121.83, 121.00, 119.03, 118.81, 118.02 (Ar), 55.34 (quat. C), 33.58, 32.61, 8.89, 8.63 (Et).

Example 3

Synthesis of Compound 2

Ir(acac)$_3$ (0.062 g, 0.13 mmol) and L$_2$ (0.22 g, 0.44 mmol) were added to glycerol (16 mL) under a N$_2$ atmosphere. The reaction temperature was heated to 220° C. for 18 h. After reaction, the mixture was cooled to room temperature and water (50 mL) was added. Then the mixture was extracted with CH$_2$Cl$_2$ (3×50 mL) and the organic phase was dried over MgSO$_4$. The solvent was removed and the residue was purified by column chromatography with CH$_2$Cl$_2$ as eluent. The product was obtained as an orange solid (0.021 g, 10%). MS (FAB): m/z 1673 (M$^+$). $^1$H NMR (CDCl$_3$): δ (ppm) 7.90 (d, J=8.1 Hz, 3H, Ar), 7.67 (d, J=5.1 Hz, 3H, Ar), 7.56-7.50 (m, 6H, Ar), 7.06-6.73 (m, 36H, Ar), 2.28 (s, 18H, Me), 1.96-1.83 (m, 12H, Et), 0.42 (t, J=7.0 Hz, 9H, Et), 0.34 (t, J=7.0 Hz, 9H, Et).

Example 4

Synthesis of Compound 3

Ir(acac)$_3$ (0.032 g, 0.065 mmol) and L$_3$ (0.12 g, 0.23 mmol) were added to glycerol (16 mL) under a N$_2$ atmosphere. The reaction temperature was heated to 220° C. for 18 h. After reaction, the mixture was cooled to room temperature and water (50 mL) was added. Then the mixture was extracted with CH$_2$Cl$_2$ (3×50 mL) and the organic phase was dried over MgSO$_4$. The solvent was removed and purified by column chromatography with CH$_2$Cl$_2$ as eluent. The product was obtained as an orange solid (0.012 g, 10%). MS (MALDI-TOF): m/z 1769 (M$^+$). $^1$H NMR (CDCl$_3$): δ (ppm) 7.90 (d, J=8.4 Hz, 3H, Ar), 7.66 (d, J=4.9 Hz, 3H, Ar), 7.55-7.51 (m, 6H, Ar), 7.03-6.65 (m, 36H, Ar), 3.77 (s, 18H, OMe), 1.92-1.82 (m, 12H, Et), 0.42 (t, J=7.3 Hz, 9H, Et), 0.34 (t, J=7.3 Hz, 9H, Et).

Example 5

Synthesis of Compound 5

Step 1

Ligand L$_1$ (0.50 g, 1.07 mmol) and IrCl$_3$.nH$_2$O (0.10 g, 54 wt.-% Ir content) were added to a mixture of 2-ethoxyethanol and water (10 mL, 3:1, v/v). The reaction mixture was stirred at 120° C. for 18 h and after cooling to room temperature, a yellow precipitate was obtained. The precipitate was collected and washed with ethanol (20 mL) and hexane (10 mL). Subsequently, the cyclometalated Ir dimer [Ir(L$_1$)$_2$Cl]$_2$ was dried under vacuum and it was finally isolated as a yellow solid (0.28 g, 85%) that was used for the next step without further purification. $^1$H NMR (CDCl$_3$): δ (ppm) 9.36 (d, J=5.4 Hz, 4H, Ar), 7.90 (d, J=8.1 Hz, 4H, Ar), 7.79-7.71 (m, 4H, Ar), 7.38 (s, 4H, Ar), 7.25-6.78 (m, 56H, Ar), 6.23 (s, 4H, Ar), 1.85-1.69 (m, 16H, Et), 0.27-0.19 (m, 24H, Et). $^{13}$C{$^1$H} NMR (CDCl$_3$): δ (ppm) 168.87, 152.25, 147.98, 146.74, 144.55, 142.91, 141.99, 141.94, 136.60, 135.83, 129.01, 123.58, 123.28, 122.17, 121.35, 120.99, 120.14, 119.28, 118.12, 117.84, 109.77 (Ar), 55.19 (quat. C), 32.82, 32.46, 8.76, 8.70 (Et).

Step 2

[Ir(L$_1$)2Cl]$_2$ (0.28 g, 0.12 mmol), Na$_2$CO$_3$ (0.12 g, 1.13 mmol) and acetylacetone (0.3 mL) were combined in 2-ethoxyethanol (16 mL) and the reaction mixture was heated to 110° C. for 18 h. After reaction, the mixture was cooled to room temperature and water (50 mL) was added. The yellow precipitate was collected, dried and purified with TLC plates using CH$_2$Cl$_2$—hexane (3:1, v/v) as eluent. The target product was obtained as an orange solid in 10% yield (0.015 g). MS (FAB): m/z 1222 (M+). 1H NMR (CDCl3): δ (ppm) 8.59 (d, J=5.4H$_z$, 2H, Ar), 7.90 (d, J=8.1H$_z$, 2H, Ar), 7.77-7.71 (m, 2H, Ar), 7.43 (s, 2H, Ar), 7.25-6.84 (m, 28H, Ar), 6.47 (s, 2H, Ar), 5.26 (s, 1H, acac), 1.90-1.73 (m, 14H, Et+Me), 0.37 (t, J=6.7 Hz, 6H, Et), 0.17 (t, J=6.7 Hz, 6H, Et). $^{13}$C{$^1$H} NMR (CDC13): δ (ppm) 184.55 (acac CO), 168.91, 152.38, 148.36, 148.02, 146.70, 146.16, 142.91, 142.36, 142.02, 136.99, 136.41, 129.02, 123.50, 123.40, 123.23, 122.15, 120.73, 120.42, 119.53, 115.36, 118.20 (Ar), 100.38 (acac CH)), 55.20 (quat. C), 32.95, 32.45 (Et), 28.83 (Me), 8.53, 8.61 (Et).

Example 6

Synthesis of Compound 9

[Ir(L$_1$)$_2$Cl]$_2$ (0.175 g, 0.075 mmol) and 4,4'-dimethyl-2,2'-dipyridyl (0.028 g, 0.15 mmol) were added to a mixture of CH$_2$Cl$_2$—MeOH (10 mL, 2:1, v/v) under a N$_2$ atmosphere. The reaction mixture was refluxed for 3 h. After being cooled to room temperature, a solution of NH$_4$PF$_6$ (0.13 g in 1 mL MeOH) was added and the mixture was stirred for 4 h until no color change was observed. The solvent was then removed under vacuum. The residue was dissolved in CH$_2$Cl$_2$ and the solution was filtered to remove the insoluble salt. After removal of the solvent, the crude product was purified by column chromatography, first eluting with CH$_2$Cl$_2$ to remove the impurity followed by elution with ethyl acetate to isolate the desired product. The product was obtained as an orange solid (0.033 g, 15%). MS (FAB): m/z 1307 (M$^+$—PF$_6^-$). $^1$H NMR (CDCl$_3$): δ (ppm) 8.56 (s, 2H, Ar), 7.78-6.10 (m, br, 42H, Ar), 7.44 (s, 1H, Ar), 7.37 (s, 1H, Ar), 7.26-6.84 (m, 30H, Ar), 2.63 (s, 6H, Me), 1.99-1.89 (m, 8H, Et), 0.42 (t, J=7.2 Hz, 6H, Et), 0.26 (t, J=7.2 Hz, 6H, Et).

Example 7

Synthesis of Compound 10

[Ir(L$_1$)$_2$Cl]$_2$ (0.15 g, 0.064 mmol) was added to CH$_2$Cl$_2$ (10 mL) under a N$_2$ atmosphere and tributylphosphine (0.5 mL) was then added. The reaction mixture was allowed to stir at room temperature for 8 h. After that, the solvent was removed under vacuum. The residue was purified by column chromatography using ethyl acetate-hexane (1:2, v/v) as eluent. The title product was obtained as a yellow solid (0.026 g, 14%). MS (FAB): m/z 1325 (M$^+$—Cl$^-$). $^1$H NMR (CDCl$_3$): δ (ppm) 9.98 (d, J=5.6 Hz, 1H, Ar), 9.01 (d, J=5.2 Hz, 1H, Ar), 7.95 (d, J=8.0 Hz, 1H, Ar), 7.87 (d, J=7.6 Hz, 1H, Ar), 7.81-7.76 (m, 2H, Ar), 7.44 (s, 1H, Ar), 7.37 (s, 1H, Ar), 7.26-6.84 (m, 30H, Ar), 6.56 (s, 1H, Ar), 6.17 (d, J=4.8 Hz, 2H, Ar), 1.89-1.72 (m, 8H, Et), 1.56-1.49 (m, 6H, Bu), 1.29-1.22 (m, 6H, Bu), 1.13-1.05 (m, 6H, Bu), 0.75 (t, J=7.2 Hz, 9H, Bu), 0.38-0.31 (m, 6H, Et), 0.09-0.02 (m, 6H, Et).

Example 8

Synthesis of Compound 11

Ir(acac)$_3$ (0.13 g, 0.27 mmol) and L$_5$ (0.50 g, 0.97 mmol) were added to glycerol (20 mL) under a N$_2$ atmosphere. The reaction temperature was heated to 220° C. for 18 h. After reaction, the mixture was cooled to room temperature and water (50 mL) was added. The mixture was then extracted with CH$_2$Cl$_2$ (3×50 mL) and the organic phase was dried over MgSO$_4$. Following this, the solvent was removed and the residue was purified by column chromatography with CH$_2$Cl$_2$-hexane (2:1, v/v) as eluent. The product was obtained as a dark red solid (0.038 g, 8%). MS (FAB): m/z 1739 (M$^+$). $^1$H NMR (CDCl$_3$): δ (ppm) 8.94 (d, J=8.9 Hz, 3H, Ar), 8.10 (s, 3H, Ar), 7.73-7.62 (m, 9H, Ar), 7.28-6.76 (m, 51H, Ar), 2.03-1.85 (m, 12H, Et), 0.53-0.43 (m, 6H, Et).

Example 9

Synthesis of Compound 15

Step 1

Under a N$_2$ atmosphere, L$_5$ (0.50 g, 0.97 mmol) and IrCl$_3$.nH$_2$O (0.13 g, 54 wt.-% Ir content) were added to 2-ethoxyethanol-water (20 mL, 3:1, v/v). The reaction mixture was stirred at 120° C. for 18 h. After it was cooled to room temperature, a red precipitate appeared. The precipitate was collected and washed with ethanol (95%, 20 mL) and hexane (10 mL). The product [Ir(L$_5$)$_2$Cl]$_2$ was dried under vacuum and obtained as a red solid (0.33 g, 70%). The product was used for the next step without further purification.

Step 2

[Ir(L$_5$)$_2$Cl]$_2$ (0.50 g, 0.20 mmol), Na$_2$CO$_3$ (1.00 g, 9.43 mmol) and acetylacetone (0.5 mL) were added to 2-ethoxyethanol (16 mL) under a N$_2$ atmosphere. The reaction temperature was kept at 110° C. for 18 h. After reaction, it was cooled to room temperature and water (50 mL) was added. The red precipitate was collected and dried. It was purified with TLC plates using CH$_2$Cl$_2$-hexane (5:1, v/v) as eluent. The product was obtained as a dark red solid (0.038 g, 7%). MS (FAB): m/z 1322 (M$^+$). $^1$H NMR (CDCl$_3$): δ (ppm) 8.96 (m, 2H, Ar), 8.50 (d, J=6.5 Hz, 2H, Ar), 8.04-7.69 (m, 8H, Ar), 7.46-7.44 (d, J=6.5 Hz, 2H, Ar), 7.24-6.91 (m, 26H, Ar), 6.77-6.73 (m, 2H, Ar), 6.58 (s, 1H, Ar), 5.25 (s, 1H, acac), 1.90-1.79 (m, 14H, Et+Me), 0.44 (t, J=7.3 Hz, 6H, Et), 0.16 (t, J=7.3 Hz, 6H, Et). $^{13}$C NMR (CDCl$_3$): δ (ppm) 184.68 (acac CO), 169.86, 152.68, 150.14, 147.94, 146.85, 144.37, 141.98, 140.80, 137.17, 136.55, 130.37, 129.00, 127.31, 127.19, 127.11, 126.15, 124.12, 123.55, 123.26, 122.17, 120.73, 119.24, 118.76 (Ar), 100.48 (acac CH), 55.27 (quat. C), 32.81, 32.59 (Et), 28.83 (Me), 8.97, 8.53 (Et).

Example 10

Synthesis of Compound 19

Step 1

Under a N$_2$ atmosphere, ligand L$_1$ (0.50 g, 1.07 mmol) and K$_2$PtCl$_4$ (0.18 g, 0.43 mmol) were added to 2-ethoxyethanol-water (15 mL, 3:1, v/v). The reaction mixture was stirred at 80° C. for 16 h. After it was cooled to room temperature, the reaction mixture was poured into water (200 mL). A yellow precipitate appeared which was collected and dried under vacuum to give [Pt(L$_1$)Cl]$_2$ as a yellow solid (0.26 g, 87%). This Pt dimer was used for the next step without further purification.

Step 2

The Pt dimer [Pt(L$_1$)Cl]$_2$ (0.40 g, 0.29 mmol), Na$_2$CO$_3$ (0.60 g, 5.66 mmol) and acetylacetone (0.2 mL) were added to 2-ethoxyethanol (10 mL) under a N$_2$ atmosphere. The reaction temperature was kept at 100° C. for 16 h. After reaction, it was cooled to room temperature and water (50 mL) was added. The yellow precipitate was collected and dried. It was purified by column chromatography with CH$_2$Cl$_2$-hexane (1:1, v/v) as eluent. The product was obtained as a bright orange solid (0.043 g, 10%). MS (FAB): m/z 759 (M$^+$). $^1$H NMR (CDCl$_3$): δ (ppm) 8.97 (d, J=5.1 Hz, 1H, Ar), 7.87-7.62 (m, 3H, Ar), 7.33-6.97 (m, 15H, Ar), 5.49 (s, 1H, acac), 2.05 (s, 3H, Me), 2.01 (s, 3H, Me), 1.97-1.87 (m, 4H, Et), 0.37 (t, J=7.3 Hz, 6H, Et). $^{13}$C NMR (CDCl$_3$): δ (ppm) 185.74, 184.10 (acac CO), 168.49, 152.04, 148.05, 147.24, 145.33, 142.88, 142.49, 137.86, 136.95, 129.12, 128.27, 123.86, 123.44, 122.40, 121.10, 120.81, 120.39, 118.99, 118.51, 117.35 (Ar), 102.51 (acac CH), 55.65 (quat. C), 32.88, 32.45 (Et), 28.30 (Me), 8.57 (Et).

Example 11

Synthesis of Compound 23

Step 1

Under a N$_2$ atmosphere, ligand L$_5$ (0.55 g, 1.07 mmol) and K$_2$PtCl$_4$ (0.18 g, 0.43 mmol) were added to 2-ethoxyethanol-water (15 mL, 3:1, v/v). The reaction mixture was stirred at 80° C. for 16 h. After it was cooled to room temperature, the reaction mixture was poured into water (200 mL). A yellow precipitate appeared which was collected and dried under vacuum to give [Pt(L$_5$)Cl]$_2$ as a yellow solid (0.25 g, 79%). This Pt dimer was used for the next step without further purification.

Step 2

[Pt(L$_5$)Cl]$_2$ (0.20 g, 0.13 mmol), Na$_2$CO$_3$ (0.80 g, 7.55 mmol) and acetylacetone (0.5 mL) were added to 2-ethoxyethanol (16 mL) under a N$_2$ atmosphere. The reaction temperature was kept at 80° C. for 18 h. After reaction, it was cooled to room temperature and water (50 mL) was added. The red precipitate was collected and dried. It was purified with TLC plates using CHCl$_3$-hexane (2:1, v/v) as eluent. The product was obtained as a dark red solid (0.024 g, 11%). MS (FAB): m/z 809 (M$^+$). $^1$H NMR (CDCl$_3$): δ (ppm) 8.85 (d, J=6.5 Hz, 2H, Ar), 8.75 (d, J=8.4 Hz, 2H, Ar), 7.94 (s, 1H, Ar), 7.86 (s, 1H, Ar), 7.73-7.57 (m, 4H, Ar), 7.28-6.90 (m, 13H, Ar), 5.42 (s, 1H, acac), 1.99-1.81 (m, 10H, Et+Me), 0.36 (t, J=7.3 Hz, 6H, Et). $^{13}$C NMR (CDCl$_3$): δ (ppm) 185.73, 183.95 (acac CO), 168.71, 152.36, 147.84, 147.46, 144.66, 143.78, 142.79, 140.39, 139.14, 137.34, 136.35, 130.83, 129.06, 127.92, 127.35, 126.19, 125.68, 123.91, 122.67, 122.44, 121.35, 120.74, 118.69, 118.51 (Ar), 102.51 (acac CH), 55.86 (quat. C), 32.96 (Et), 28.44, 27.35 (Me), 8.79 (Et).

Example 12

Photophysical, Redox and Thermal Properties

The UV-vis and photoluminescence data of 1 and 5 are listed in Table 1. The intense absorption bands (log ε-4.7-4.9) at ca. 309-375 for 1 and ca. 297-387 nm for 5 appear to be ligand-based transitions that closely resemble the spectra of the free ligand $L_1$, and are assigned to the spin-allowed $^1\pi$-$\pi$* transitions associated with the arylamino and aminofluorenyl fragments. Similar absorption features were also observed in the spectra of $Ar_2$—N—$C_6H_4$—X compounds near 300 and 350 nm. The bands are also accompanied by weaker, lower energy features extending into the visible region from 410 to 480 nm that correspond to excitation to $^1$MLCT, $^3$MLCT and $^3\pi$-$\pi$* lowest states. With reference to previous spectroscopic data for other cyclometalated iridium complexes in the literature, complexes 1 and 5 possess the dominantly $^3\pi$-$\pi$* lowest excited states. Both iridium complexes show strong room-temperature phosphorescence ($\lambda_{em}$ in $CH_2Cl_2$=555 and 564 nm for 1 and 5, respectively) from the predominantly ligand-centered $^3\pi$-$\pi$* excited state and these emission bands experience large Stokes shifts (>100 nm). The vibronic splitting of ca. 1165 cm$^{-1}$ ($v_{0-1}$) in the emission profile corresponds to the aromatic stretching of the cyclometalated ligands which is diagnostic of the involvement of the intra-ligand π-π* transitions in the emission, and these vibronic fine structures preclude the assignment of $^3$MLCT states that are usually broad and featureless. Both the absorption and phosphorescence spectra of 1 are located at wavelengths ($\lambda_{abs}$=375, 415, 478 nm, $\lambda_{em}$=555 nm) longer than those of the corresponding iridium compound without the diphenylamino units [Ir(Flpy)$_3$] ($\lambda_{abs}$=321, 336, 405 nm, $\lambda_{em}$=545 nm). The introduction of an electron-donating diphenylamino group into the electron-deficient pyridine moiety of the ligand is expected to increase the donor-acceptor (D-A) character of the ligand. It is clear that the phosphorescence spectrum of 1 is red-shifted when their ligands have a larger π-conjugation spacer and/or strong intramolecular D-A interaction. Complex 1 has a very similar emission pattern to 5. The phosphorescence quantum yields, $\phi_P$, in degassed $CH_2Cl_2$ solutions are moderate at 0.12 and 0.13 for 1 and 5, respectively, relative to a fac-[Ir(ppy)$_3$] standard ($\phi_P$=0.40, Hppy=2-phenylpyridine). The observed phosphorescence lifetimes, $\tau_P$, have a magnitude of about 0.08-0.11 μs in $CH_2Cl_2$. Accordingly, the radiative lifetimes ($\tau_r$) of the triplet excited state deduced from $\tau_r=\tau_P/\phi_P$ are as short as 0.67-0.85 μs, which correlates well with the unusually large extinction coefficients measured for the $^3$MLCT bands. In the solid state, the lifetime is even shorter (0.05-0.08 μs), possibly due to the phosphorescence self-quenching associated with molecular packing. The triplet radiative and nonradiative rate constants, $k_r$ and $k_{nr}$, are calculated from $\phi_P$ and $\tau_P$ using the relationships $\phi_P=\phi_{ISC}\{k_1/(k_r+k_{nr})\}$ and $\tau_P(k_r+k_{nr})^{-1}$. Here, $\phi_{ISC}$ is the intersystem-crossing yield which can be safely assumed to be 1.0 for iridium complexes because of the strong spin-orbit interaction caused by the heavy-atom effect of iridium. Complexes 1 and 5 have similar $k_r$ values, as can be expected from the comparable quantum efficiencies and lifetimes of both compounds.

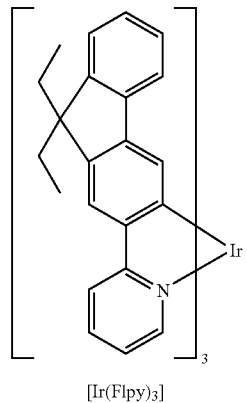

[Ir(Flpy)$_3$]

From cyclic voltammetry experiments, complexes 1 and 5 show two reversible anodic redox couples with potentials in the range of 0.15-0.53 V, corresponding to the sequential removal of electrons from the peripheral arylamino group and Ir-phenyl center (Table 2 below).

TABLE 2

| Complex | $E_{1/2}^{ox}$ [V][a] | $E_{1/2}^{red}$ [V][a] | HOMO [eV] | LUMO [eV] | $T_{dec}$ [° C.][b] | $T_g$ [° C.] |
|---|---|---|---|---|---|---|
| 1 | 0.15, 0.45 | −1.87 | −4.95 | −2.93 | 473 | 160 |
| 5 | 0.26, 0.53 | −1.67 | −5.06 | −3.13 | 432 | 153 |

[a]0.1 M [Bu$_4$N]PF$_6$ in CH$_2$Cl$_2$, scan rate 100 mV s$^{-1}$, versus Fc/Fc$^+$ couple.
[b]Onset decomposition temperature.

The reversible reduction occurs primarily on the heterocyclic portion of the C^N ligand with potentials spanning from −1.67 to −1.87 V. Notably, the incorporation of NPh$_2$ groups to the fluorene core caused a negative shift in the anodic $E_{1/2}$ by ca. 80 mV as observed by changing from [Ir(Flpy)$_3$] (+0.23 V) to 1. On the basis of the redox data, we can estimate the HOMO and LUMO energy levels of 1 and 5 with reference to the energy level of ferrocene (4.8 eV below the vacuum level) and the first oxidation potentials were used to determine the HOMO energy levels. The HOMO and LUMO levels for 1 and 5 match closely with the energy levels for NPB (HOMO: −52 eV) and TPBI (LUMO: −2.9 eV). The LUMO levels of both complexes (−2.93 and −3.13 eV) are lower than that of 2-(4-biphenylyl)-5-(4-tert-butylphenyl)-1,3,4-oxadiazole (PBD, −2.4 eV), one of the most widely used hole-blocking/electron-transport (HB/ET) material and comparable to that of tris(8-hydroxyquinolinato)aluminium (Alq$_3$, −3.0 eV). When the diphenylamino end groups are attached to the fluorene rings, the HOMO value of is raised to −4.95 eV relative to the vacuum level. Complex 1 can show elevated HOMO energy levels as compared to [Ir(Flpy)s] (−5.02 eV), indicating that compound 1 is more electropositive (or has a lower ionization potential) than [Ir(Flpy)$_3$], and a better HT ability in 1 can be expected.

Example 13

Electrophosphorescent OLEDs Fabricated from 1, 5, 9 and 19

Commercial indium tin oxide (ITO) coated glass with sheet resistance of 20-30Ω/□ was used as the starting substrate. Before device fabrication, the ITO glass substrates were cleaned by ultrasonic baths in organic solvents followed by ozone treatment for 10 min. Each device was assembled in the following sequence: ITO on glass substrate (anode), 75 nm of NPB, 20 nm of the emitting layer made of CBP host and phosphorescent dopant (x %), 45 nm of TPBI, 1 nm of LiF and 60 nm of Al (cathode). The organic layers were evaporated and laminated in the above sequence under $4 \times 10^{-4}$ Pa without breaking vacuum between each vacuum deposition process. The emissive layer was formed by co-deposition of the dopant and the host. The evaporation rates were 1~2, 0.3, and 4~6 Å/s for organic materials, LiF and aluminum, respectively. The layer thickness was monitored in situ using a quartz crystal oscillator. The active area of the device was 5 mm² as defined by the shadow mask. The electrical and optical characteristics of these devices were measured using R6145 DC voltage current source, FLUKE 45 dual display multimeter and Spectrascan PR650 spectrophotometer in a dark room under ambient air conditions. In a representative embodiment of the present invention, OLED devices A-I were fabricated using 1, 5, 9 and 19 as emissive dopants (Table 3).

We note that there is no voltage dependence of the EL spectra from 6 V to 12 V and the maximum EL peak is independent of the guest concentration. Essentially, the devices A-C comprising phosphor 1 exhibit strong EL peak at about 564 nm with low turn-on voltages ($V_{turn-on}$) for light emission at I cd/m² of 3.8-4.2 V and Commission Internationale de L'Eclairage (CIE) color coordinates of (0.50, 0049) with a color saturation of about 93%. The EL devices D-F containing dopant 5 turned on at ~5 V with a prominent EL emission at ~572 nm and the CIE color coordinates at (0.55, 0045) correspond to the orange region of the CIE chromaticity diagram. In each case, the EL spectrum resembles its corresponding PL spectrum from thin film, which indicates that both EL and PL arise from the same excited state or the same type of exciton.

The luminance reached 7793-8314 cd/m2 at 11.5-12.0 V for devices A-C, and 6594-8213 cd/m2 at 12.0 V for devices D-F. Although phosphors 1 and 5 have similar PL quantum yields and lifetimes in solution, the peak EL efficiencies of the devices fabricated from 5 are notably inferior to those of the devices based on I for a given doping level. We ascribe this

TABLE 3

| Device | Phosphor dopant | $V_{turn-on}$ [V] | Luminance L [cd/m²] | $\eta_{ext}$ [%] | $\eta_L$ [cd/A] | $\eta_p$ [lm/W] | $\lambda_{max}$ [nm][c] |
|---|---|---|---|---|---|---|---|
| A | 1 (5 wt.-%) | 4.2 | 2740[a] | 4.58 | 13.81 | 4.08 | 564 |
|   |   |   | 8283 (12)[b] | 9.89 (4.5) | 29.77 (4.5) | 20.78 (4.5) | (0.50, 0.49) |
| B | 1 (8 wt.-%) | 4.2 | 2570[a] | 4.36 | 13.02 | 4.56 | 564 |
|   |   |   | 7793 (11.5)[b] | 8.23 (5.0) | 24.73 (5.0) | 15.54 (5.0) | (0.50, 0.49) |
| C | 1 (10 wt.-%) | 3.8 | 2497[a] | 4.22 | 12.66 | 4.46 | 564 |
|   |   |   | 8314 (12)[b] | 7.72 (4.5) | 23.24 (4.5) | 16.23 (4.5) | (0.50, 0.49) |
| D | 5 (5 wt.-%) | 5.6 | 2158[a] | 4.25 | 10.42 | 3.06 | 572 |
|   |   |   | 8213 (12)[b] | 7.89 (7.0) | 19.26 (7.0) | 11.22 (6.0) | (0.55, 0.45) |
| E | 5 (8 wt.-%) | 4.6 | 1910[a] | 3.92 | 9.56 | 2.84 | 572 |
|   |   |   | 7673 (12)[b] | 7.66 (5.0) | 18.53 (5.0) | 11.64 (5.0) | (0.55, 0.45) |
| F | 5 (10 wt.-%) | 4.7 | 1305[a] | 2.79 | 6.71 | 1.91 | 572 |
|   |   |   | 6594 (12)[b] | 5.78 (5.5) | 13.65 (5.5) | 8.45 (5.0) | (0.55, 0.44) |
| G | 9 (5 wt.-%) | 3.5 | 1507[a] | 2.47 | 7.53 | 3.36 | 560 |
|   |   |   | 15611 (12)[b] | 6.48 (3.4) | 19.71 (3.4) | 18.39 (3.3) | (0.44, 0.47) |
| H | 19 (10 wt.-%) | 8.4 | 1609[a] | 3.49 | 8.09 | 2.06 | 572 |
|   |   |   | 4195 (15)[b] | 6.64 (7.5) | 15.41 (7.5) | 7.07 (6.5) | (0.54, 0.45) |
| I | 19 (10 wt.-%) | 6.7 | 946[a] | 1.95 | 4.96 | 1.23 | 572 |
|   |   |   | 3371 (15)[b] | 4.19 (8.5) | 10.03 (8.5) | 3.71 (8.5) | (0.55, 0.45) |

[a]Values collected at 20 mA/cm².
[b]Maximum values of the devices. Values in parentheses are the voltages at which they were obtained.
[c]CIE coordinates [x, y] in parentheses.

Figure 12:
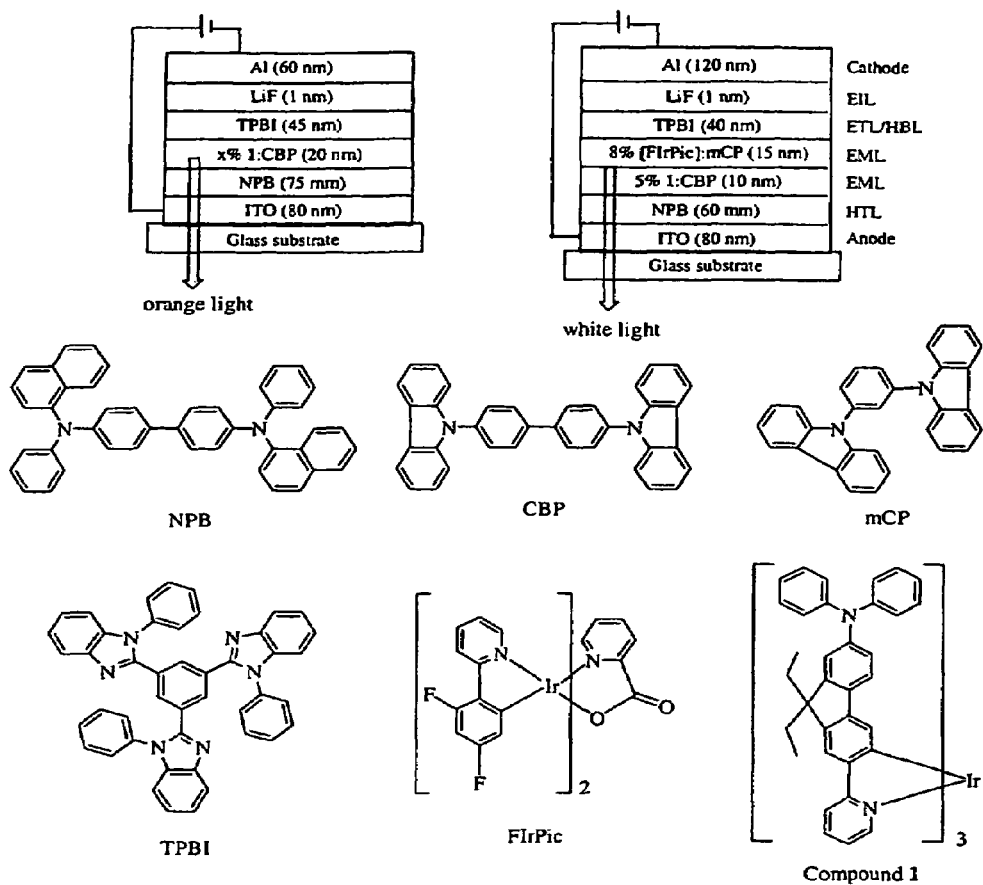
FIG. 12 shows the general structures for electrophosphorescent OLED and WOLED devices and the molecular structures of the compounds used in making these devices.
Figure 13:
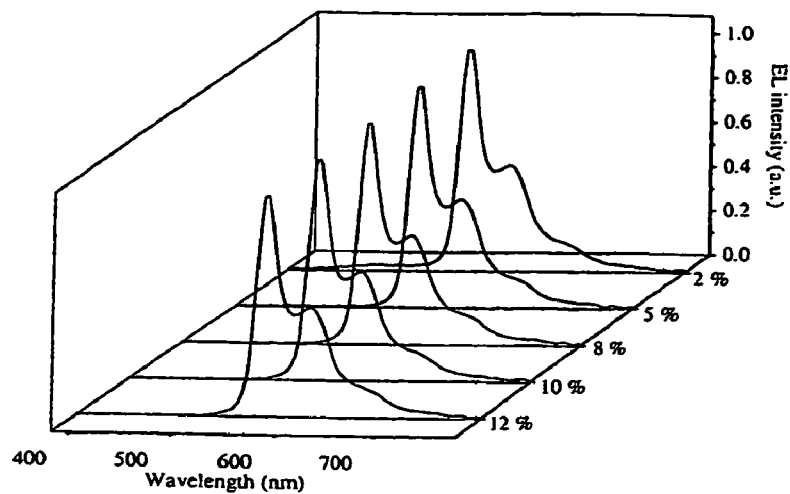
FIG. 13 shows the EL spectra of compound I-doped OLEDs at different dopant concentrations.
Figure 14:
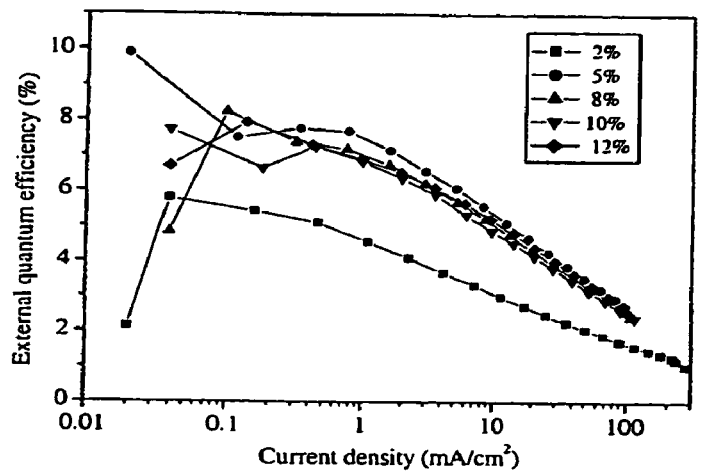
FIG. 14 shows the external, quantum efficiency vs. the current density in OLEDs at different dopant concentrations of compound I.
Figure 15:
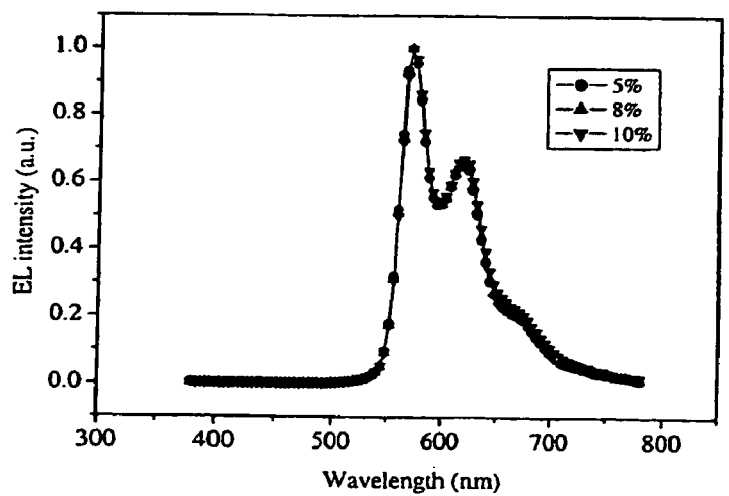
FIG. 15 shows the EL spectra of compound 5-doped OLEDs at different dopant concentrations.
Figure 16:
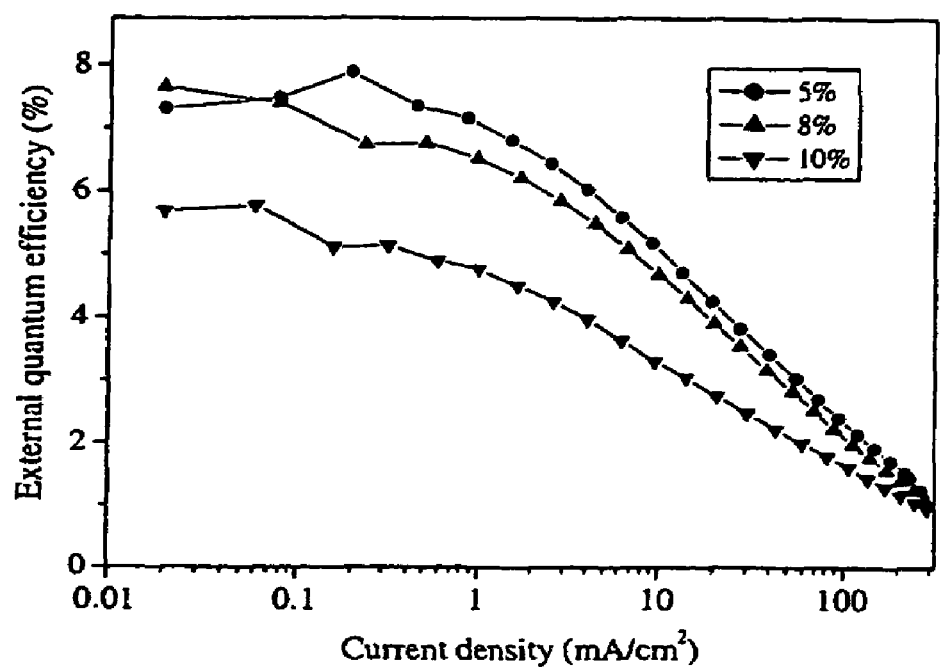
FIG. 16 shows the external quantum efficiency vs the current density in OLEDs at different dopant concentrations of compound 5.

FIG. 12 exemplifies the device structures and the molecular structures of the materials used in our devices for the electrophosphor 1. The structure consists of NPB as the hole transport layer (HTL), CBP doped with 1 as the emission layer (EML), TPBI as both the electron transport and hole blocking layer (ETL/HBL), LiF as the electron injection layer (EIL) and Al as the cathode. To optimize the device efficiency, the thickness of each layer was first fixed (HTL 75 nm, EML 20 nm and ETL 45 nm), while the doping concentration of 1 was changed from 2 wt.-% to 12 wt.-%. In the present work, no emission from CBP was observed even at high current density, indicating a complete energy transfer from the host exciton to the phosphor molecule. The performance of the phosphorescence-based OLEDs A-I is remarkable and the relevant information are listed in Table 3. The electroluminescence (EL) spectra at a driving voltage of 8 V and the external quantum efficiency as a function of current density of 1-doped devices are shown in FIGS. 13 and 14, respectively, whereas those for 2-doped devices are depicted in FIGS. 15 and 16.

higher efficiency to the more amorphous behavior of I (Tg 160° C. versus 153° C. for 5), which shows improved chemical compatibility of I with the CBP host and leads to a more homogeneous distribution of this Ir dopant in CBP. Device A furnished a maximum external quantum efficiency (next) of 9.89%, a luminance efficiency ($\eta$L) of 29.77 cd/A and a power efficiency ($\eta$p) of 20.78 lm/W at 0.02 mA/cm2. For devices B and C, the corresponding peak efficiencies are $\eta$ext=8.23%, $\eta$L=24.73 cd/A and $\eta$p=15.54 lm/W, and $\eta$ext=7.72%, $\eta$L=23.24 cd/A and $\eta$p=16.23 lm/W, respectively. For 5, the highest values achieved for $\eta$ext, $\eta$L and $\eta$p at the 5 wt.-% guest concentration (device D) are 7.89%, 19.26 cd/A and 11.22 lm/W, respectively and the EL efficiency data for devices E and F are tabulated in Table 3. At the low concentrations, the $\eta$ext value increases with increasing concentrations of dopants. At high concentrations beyond 5 wt.-%, $\eta$ext tends to decrease, probably as a consequence of concentration quenching and the maximum $\eta$ext was achieved at 5 wt.-% concentration.

Figure 17:
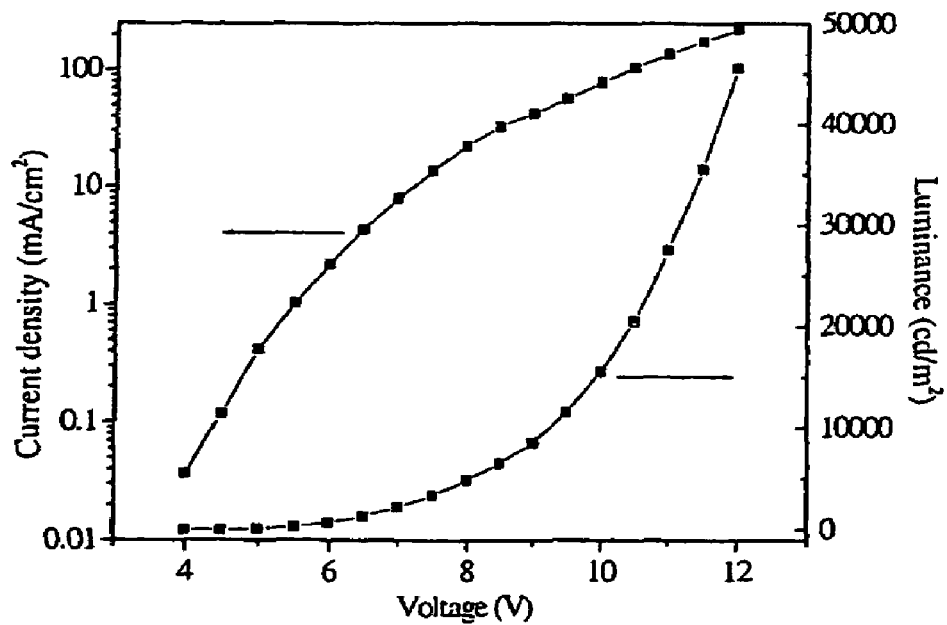
FIG. 17 shows the J-V-L curves in an optimized OLED device using 5 wt.-% of compound I.

With the doping concentration of 1 kept fixed at 5 wt.-%, the thicknesses of HTL, EML and ETL were varied to optimize the OLED devices. Optimization experiments found that the device had the best performance at the thicknesses of 55, 25 and 40 nm for NPB, dopant and TPBI layers, respectively. It was found that the best performance was obtained for the devices with 55 nm, 25 nm and 40 nm for the three layers, respectively. Given these considerations, the J-V-L characteristics and external quantum efficiency versus current density curve of the optimized device are shown in FIG. 17. A luminance of 4800 cd/m$^2$ can be achieved at 8 V and the highest luminance efficiency attainable is 34.8 cd/A at 1 mA/cm$^2$ and 6 V.

Device G comprising phosphor 9 exhibits a strong EL peak at about 560 nm (CIE coordinates: x=0.44, y=0.47) with a very low turn-on voltage of 3.5 V and a luminance of up to ~15600 cd/m2 can be achieved at 12 V. The peak efficiencies are ηext=6.48%, ηL=19.71 cd/A and ηp=18.39 lm/W for this device. For the platinum(II)-based phosphor 19, devices H and I were fabricated in which they contain different hosts for the electrophosphorescent emission. Device H using the CBP host is shown to give higher E.L efficiencies than device I based on mCP and the corresponding peak efficiencies are ηext=6.64%, ηL=15.41 cd/A and ηp=7.07 lm/W for the former, and ηext=4.19%, ηL=10.03 cd/A and ηp=3.71 lm/W for the latter.

Example 14

White Organic Light-Emitting Devices Based on Phosphor 1

The orange color emitted from this device can be mixed with the blue light to make dual emissive layers WOLEDs with the device structure depicted in FIG. 12. The WOLED device employs two emission layers in which one layer contains 5 wt.-% 1 doped in the CBP host matrix and another layer composes of the mCP host (mCP=N,N'-dicarbazolyl-3,5-benzene) doped with a 8 wt.-% blue-emitting phosphorescent material FIrPic (iridum(III)bis(4,6-di-fluorophenyl)-pyridinato-N, C$^2$) picolinate). The WOLED consists of the HTL, EML and ETL as before. Here, the EML is made up of two independent layers: FIrPic doped in mCP host for the blue light, and 1 doped CBP for the orange light. The layer thicknesses of HTL, ETL and cathodes were kept to be the same throughout. The effect of the evaporation sequence of the two emission layers was also examined for optimal results. If the blue emissive layer was evaporated before the orange emissive layer, the EL spectrum of the whole device had a much higher peak in the orange range than in the blue region and the CIE white balance was not good. This means that the energy transfer from mCP to FIrpic is incomplete if no hole blocking layer is deposited next to it. The holes are then easily transported from the blue-emitting layer to the orange-emitting layer. In other words, the recombination process should preferably be completed in the orange emission layer than in the blue emission layer. If the evaporation sequence for the EML layers is reversed in order, we could get WOLEDs with satisfactory electrical and optical performance. So it is desirable to deposit the orange emission layer first, followed by the blue emission layer in the fabrication process.

Figure 18:
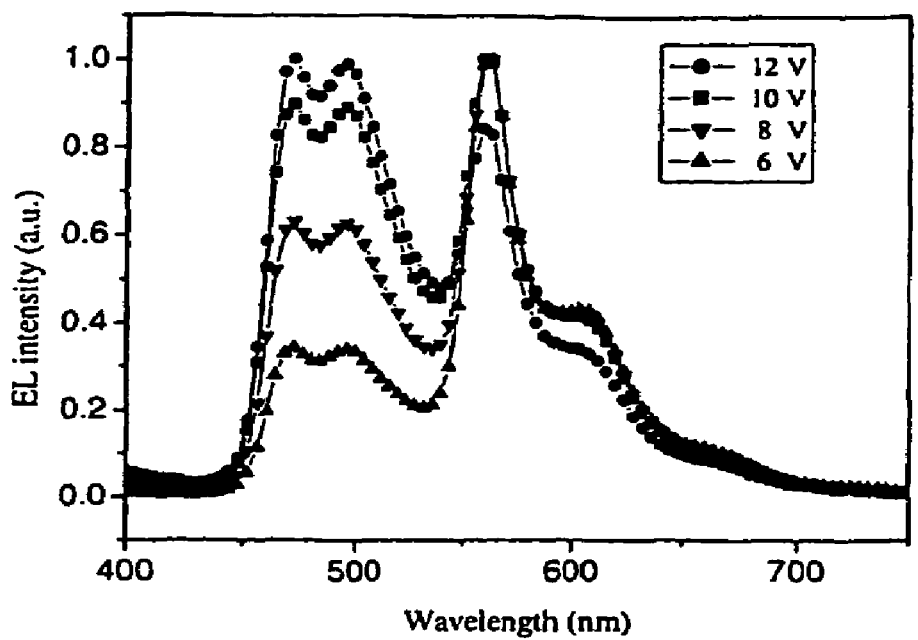
FIG. 18 shows the EL spectra of the electrophosphorescent WOLED device at different voltages: 6 V (▲), 8 V (▼), 10 V (■), and 12 V (●).
Figure 19:
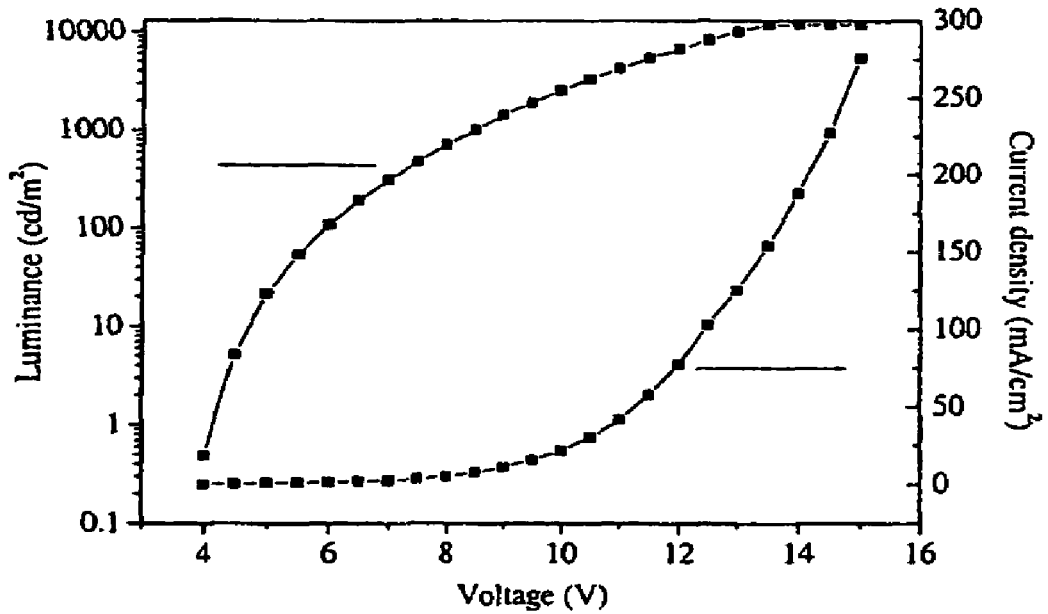
FIG. 19 shows the J-V-L characteristics of the electrophosphorescent WOLED device of the present invention.

In order to get the best white light performance, the thickness of each of the two emissive layers was adjusted carefully. It was found that a thickness of 10 nm and 15 nm for the red and blue emission layer, respectively, afforded the best results. It is clear from FIG. 18 that when the applied voltage is 10 V, the EL spectrum exhibits two close peaks at 472 nm and 496 nm, which arise from FIrPic and a sharp peak at 560 nm due to the orange light from the triplet excited state of 1. FIG. 19 shows the measured J-V-L curves of this device. The color of the white light corresponds to the CIE coordinates of (0.31, 0.41) and a strong voltage dependence of the EL spectrum is observed, with the blue color increasing relative to the orange dopant at increasing voltages. This can be rationalized by the fact that the holes have higher mobilities under higher electrical field condition and they will drift to the blue recombination region without being completely recombined in the orange-emitting layer. So, the contribution due to the blue light becomes more significant at higher voltages. The threshold voltage of the WOLED device is about 4.2 V and the luminance reaches 3200 cd/m$^2$ at 10 V and 30 mA/cm$^2$. The maximum current and power efficiencies of 17.8 cd/A and 7.6 lm/W for the WOLED device are achieved at 8 V and 1 mA/cm$^2$.

REFERENCES

The following publications are incorporated herein by reference as illustrative of the state of the art:

[1] Tsutsui et al., "High Quantum Efficiency in Organic-Emitting Devices with Iridium-Complex as a Triplet Emissive Center," *Jpn. J. Appl. Phys*. December 1999, 38(12B), L1502-L1504.

[2] Baldo et al., "Highly Efficient Phosphorescent Emission from Organic Electroluminescent Devices," *Nature*. September 1998, 395, 151-153.

[3] Wu et al., "Tuning the Emission and Morphology of Cyclometalated Iridium Complexes and Their Applications to Organic Light-Emitting Diodes," *J. Mater. Chem*. 2005, 15, 1035-1042.

[4] Xie et al., "Reduction of Self-Quenching Effect in Organic Electrophosphorescence Emitting Devices via the Use of Sterically Hindered Spacers in Phosphorescence Molecules," *Adv. Mater*. August 2001, 13(16), 1245-1248.

[5] Nazeerudin et al., "Highly Phosphorescence Iridium Complexes and Their Application in Organic Light-Emitting Devices," *J. Am. Chem. Soc*. 2003, 125(29), 8790-8797.

[6] Tsuzuki et al., "Color Tunable Organic Light-Emitting Diodes Using Pentafluorophenyl-Substituted Iridium Complexes," *Adv. Mater*. September 2003, 15(17), 1455-1458.

[7] Gong et al., "Electrophosphorescence from a Polymer Guest-Host System with an Iridium Complexes as Guest: Forster Energy Transfer and Charge Trapping," *Adv. Funct. Mater* June 2003, 13(6), 439-443.

[8] Gong et al., "Electrophosphorescence from a Conjugated Copolymer Doped with an Iridium Complex: High Brightness and Improved Operational Stability," *Adv. Mater* January 2003, 15(1), 45-49.

[9] Lamansky et al., "Synthesis and Characterization of Phosphorescent Cyclometalated Iridium Complexes," *Inorg. Chem*. March 2001, 40(7), 1704-1711.

[10] Kwong et al., "High Operational Stability of Electrophosphorescent Devices," *Appl. Phys. Lett.* July 2002, 81(1), 162-164.
[11] Kavitha et al., "In Search of High-Performance Platinum Phosphorescent Materials for the Fabrication of Red Electroluminescent Devices," *Adv. Funct. Mater* February 2005, 15(2), 223-229.
[12] Baldo et al., "Phosphorescent Materials for Application to Organic Light Emitting Devices," *Pure Appl. Chem.* 1999, 71(11), 2095-2106.
[13] Adachi et al., "Nearly 100% Internal Phosphorescence Efficiency in an Organic Light Emitting Devices," *J. Appl. Phys.* November 2001, 90(10), 5048-5051.
[14] Adamovich et al., "Highly Efficiency Single Dopant White Electrophosphorescent Light Emitting Diodes," *New J. Chem.* 2002, 15, 1171-1178.
[15] D'Andrade et al., "Efficient Organic Electrophosphorescent White-Light-Emitting Device with a Triple Doped Emissive Layer," *Adv. Mater.* April 2004, 16(7), 624-628.
[16] D'Andrade et al., "Controlling Exciton Diffusion in Multilayer White Phosphorescent Organic Light Emitting Devices," *Adv. Mater.* January 2002, 14(2), 147-151.
[17] Furuta et al., "Platinum-Functionalized Random Copolymers for Use in Solution-Processible Efficient, Near-White Organic Light-Emitting Diodes," *J. Am. Chem. Soc.* 2004, 126(47), 15388-15389.
[18] Adachi et al., "Highly-Efficiency Red Electrophosphorescent Devices," *Appl. Phys. Lett.* March 2001, 78(11), 1622-1624.
[19] Markham et al., "Highly-Efficiency Green Phosphorescence from Spin-coated Single-Layer Dendrimer Light-Emitting Diodes," *Appl. Phys. Lett.* April 2002, 80(15), 2645-2647.
[20] Huang et al., "Highly Phosphorescent Bis-Cyclometalated Iridium Complexes Containing Benzoimidazole-Based Ligands," *Chem. Mater.* 2002, 16(12), 2480-2488.
[21] Su et al., "Highly Efficient Red Electrophosphorescent Devices Based on Iridium Isoquinoline Complexes: Remarkable External Quantum Efficiency Over a Wide Range of Current," *Adv. Mater.* June 2003, 15(11), 884-888.
[22] Rayabarapu et al., "New Iridium Complexes with Cyclometalated Alkenylquinoline Ligands as Highly Efficient Saturated Red-Light Emitters for Organic Light-Emitting Diodes," *Adv. Mater* June 2005, 17(3), 349-353.
[23] Lamansky et al., "Highly Phosphorescent Bis-Cyclometalated Iridium Complexes: Synthesis, Photophysical Characterization, and Use in Organic Light Emitting Diodes," *J. Am. Chem. Soc.* 2001, 123(18), 4304-4312.
[24] Duan et al., "New Iridium Complexes as High Efficient Orange-Red Emitters in Organic Light-Emitting Diodes," *Adv. Mater.* February 2003, 15(3), 224-229.
[25] Okada et al., "Substituent Effects of Iridium Complexes for Highly Efficient Red OLEDs," *Dalton Trans.* 2005, 1583-1590.
[26] Wong, W. Y., "Metallated Molecular Materials of Fluorene Derivatives and their Analogues," *Coord. Chem. Rev.* 2005, 249, 971-997.

The references and patents cited herein are incorporated by reference.

What is claimed is:

1. A diarylaminofluorene chromophore compound having the following structure:

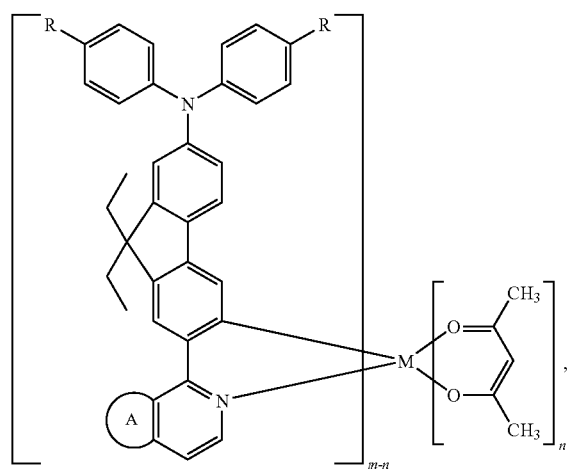

wherein:
M is a metal atom of Ir, Pt;
R is H, or $CH_3$, $OCH_3$, or F;
A is none or six-member carbocyclic aromatic ring system; and
m is 3 and n is 0 or m is 3 and n is 1 when M is Ir;
and m is 2 and n is 1 when M is Pt.

2. The diarylaminofluorene chromophore compound of claim 1, wherein the compound has the structure:

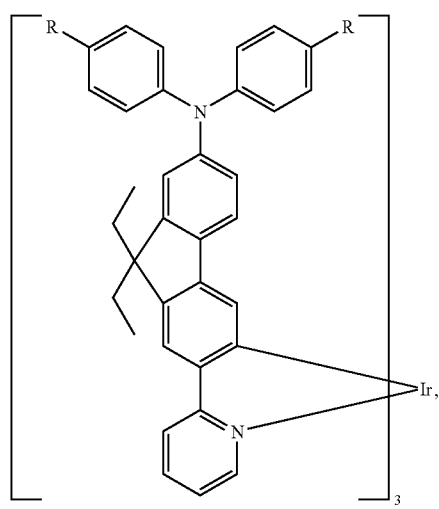

and wherein R is H, $CH_3$, $OCH_3$, or F.

3. The diarylaminofluorene chromophore compound of claim 1, wherein the compound has the structure:

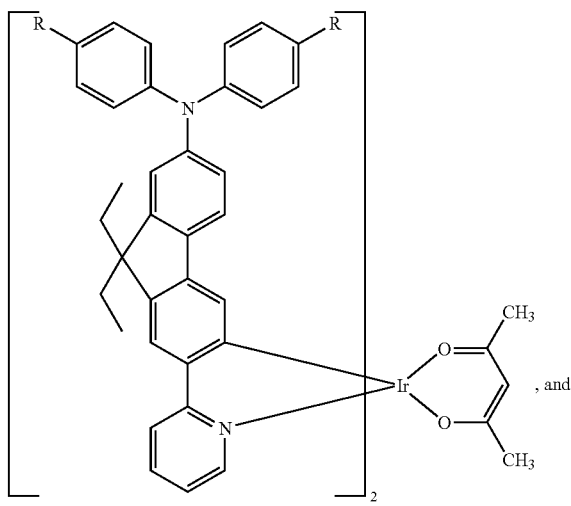

wherein R is H, CH$_3$, OCH$_3$, or F.

4. The diarylaminofluorene chromophore compound of claim 1, wherein the compound has the structure:

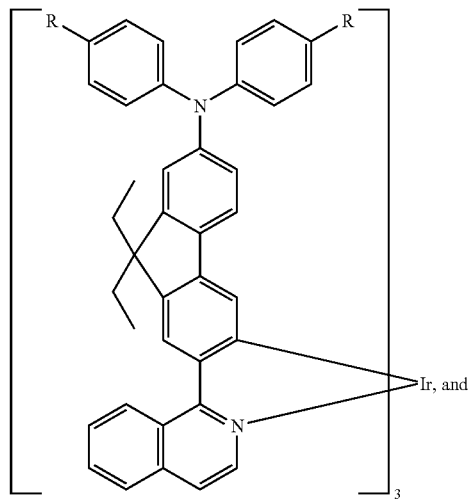

wherein R is H, CH$_3$, OCH$_3$, or F.

5. The diarylamlnofluorene chromophore compound of claim 1, wherein the compound has the structure:

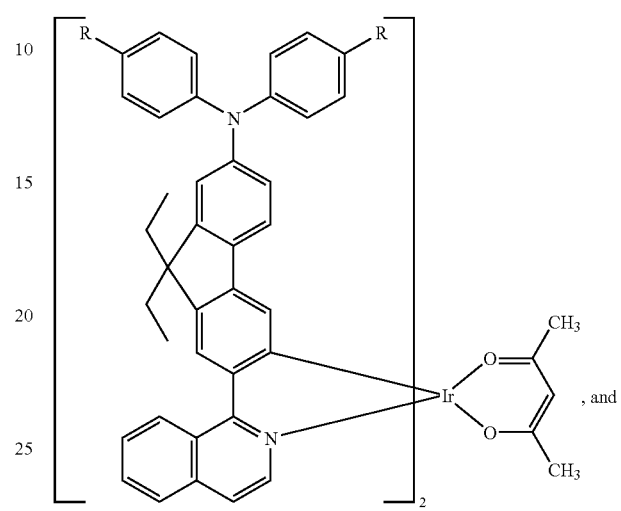

wherein R is H, CH$_3$, OCH$_3$, or F.

6. The diarylaminofluorene chromophore compound of claim 1, wherein the compound has the structure:

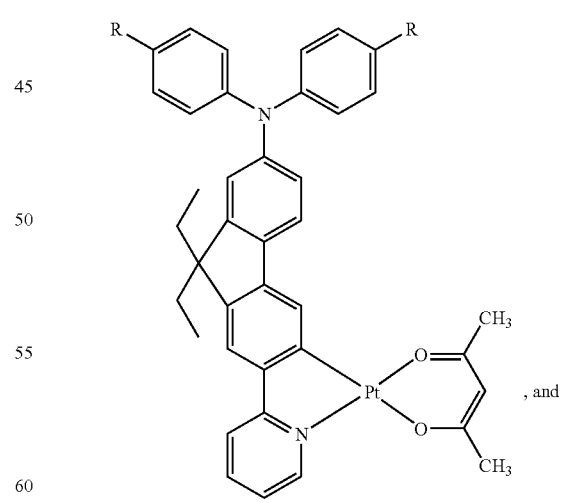

wherein R is H, CH$_3$, OCH$_3$ or F.

7. The diarylaminofluorene chromophore compound of claim 1, wherein the compound has the structure:

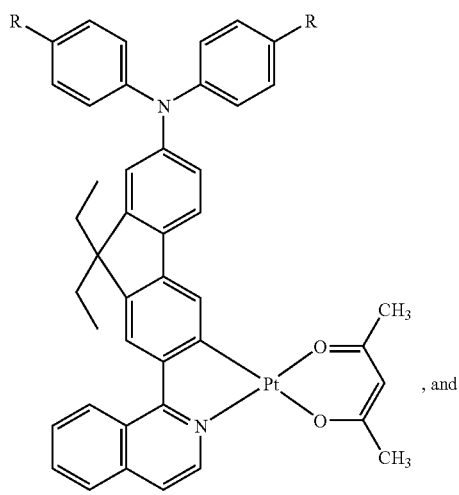

wherein R is H, CH$_3$, OCH$_3$, or F.

8. A diarylaminofluorene chromophore compound, having the following structure:

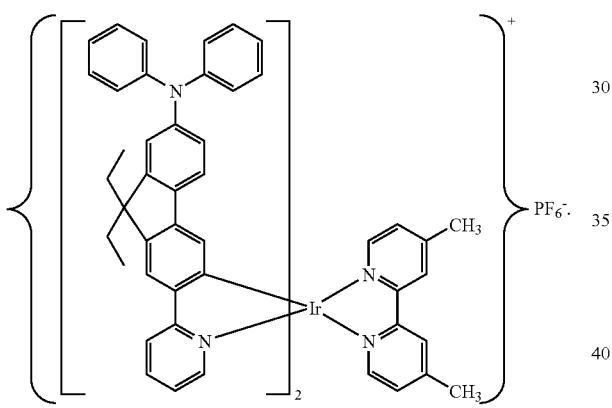

9. A diarylaminofluorene chromophore compound having the following structure:

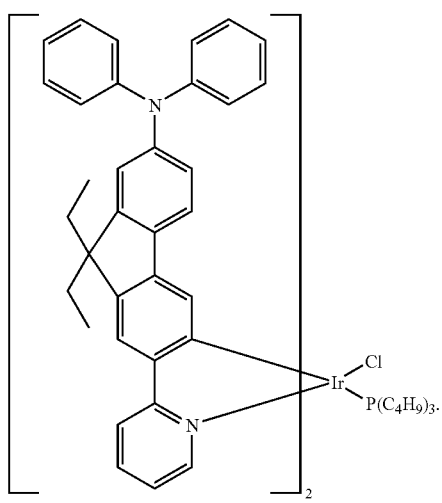

10. An organic light-emitting device, comprising:
(a) an anode;
(b) a cathode; and
(c) an emissive layer disposed between the anode and the cathode, wherein the emissive layer comprises an emissive material including a compound having the structure:

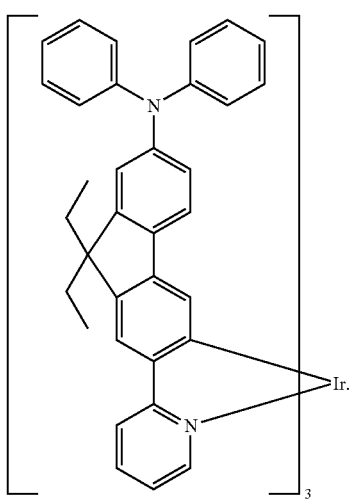

11. The organic light-emitting device of claim 10, wherein the emissive layer comprises CBP host material doped with emissive material comprising from about 2 to about 12 wt.-% of the emissive layer.

12. An organic light-emitting device, comprising:
(a) an anode;
(b) a cathode; and
(c) an emissive layer disposed between the anode and the cathode, wherein the emissive layer comprises an emissive material including a compound having the structure of claim 3 wherein R is H.

13. The organic light-emitting device of claim 12, wherein the emissive layer comprises a CBP host material doped with an emissive material comprising from about 1 to about 10 wt.-% of the emissive layer.

14. An organic light-emitting device, comprising:
(a) an anode;
(b) a cathode; and
(c) an emissive layer disposed between the anode and the cathode, wherein the emissive layer comprises an emissive material including a compound having the structure of claim 6 wherein R is H.

15. The organic light-emitting device of claim 14, including CBP host material doped with 10 wt.-% of emissive material.

16. The emissive material of claim 14, including mCP host material doped with from about 1 to about 12 wt.-% of emissive material.

17. A white organic light-emitting device, comprising:
(a) an anode;
(b) a cathode; and
(c) an emissive layer disposed between the anode and the cathode, wherein the emissive layer comprises an emissive material including a compound having the structure of claim 2 wherein R is H, and a blue phosphor Fir-Pic.

18. An organic light-emitting device, comprising:
(a) an anode;
(b) a cathode; and
(c) an emissive layer disposed between the anode and the cathode, wherein the emissive layer comprises an emissive material including a compound having the structure of claim 8.

19. An organic light-emitting device, comprising:
(a) an anode;
(b) a cathode; and
(c) an emissive layer disposed between the anode and the cathode, wherein the emissive layer comprises an emissive material including a compound having the structure of claim 9.

* * * * *

UNITED STATES PATENT AND TRADEMARK OFFICE
CERTIFICATE OF CORRECTION

PATENT NO. : 7,652,136 B2
APPLICATION NO. : 11/520148
DATED : January 26, 2010
INVENTOR(S) : Hoi-Sing Kwok et al.

It is certified that error appears in the above-identified patent and that said Letters Patent is hereby corrected as shown below:

On the cover sheet of patent page 1, column 1, next to last line, "Adv. Mater." should read --*Adv. Mater.*--;

On the cover sheet of patent page 1, column 2, line 6, "J. Am. Chem Soc." should read --*J. Am. Chem. Soc.*--;

On the cover sheet of patent page 1, column 2, In the Abstract, line 5, "R is H, CH3, OCH3, or F" should read --R is H, $CH_3$, $OCH_3$, or F--;

On the cover sheet of patent page 1, column 2, In the Abstract, line 7, "$0 \geq m \geq 3$" should read --$3 \geq m \geq 0$--;

On the cover sheet of patent page 1, column 2, In the Abstract, line 8, "$0 \geq n \geq 1$" should read --$1 \geq n \geq 0$--;

On the cover sheet of patent page 2, column 1, last line, "*Pys.*" should read --*Phys.*--;

On the cover sheet of patent page 2, column 2, last reference, first line "triplet" should read --Triplet--;

In the Specification at column 2, line 61,
"as N,N'-diphenyl-N,N'-bis(3-methylphenyl1)-[1,1'-biphenyl]-" should read
--as *N,N'*-diphenyl-*N,N'*-bis(3-methylphenyl1)-[1,1' -biphenyl]- --

In the Specification at column 5, line 51, "I-doped" should read --1-doped--;

In the Specification at column 5, line 55, "compound I" should read --compound 1--;

In the Specification at column 5, line 63, "compound I" should read --compound 1--;

In the Specification at column 8, line 4, "$IrCl_3.nH_2o$" should read --$IrCl3 \cdot nH_2O$--;

Signed and Sealed this
Twenty-first Day of June, 2011

David J. Kappos
*Director of the United States Patent and Trademark Office*

CERTIFICATE OF CORRECTION (continued)

U.S. Pat. No. 7,652,136 B2

In the Specification at column 8, line 7, "platinum III" should read --platinum II--;

In the Specification at column 8, line 11, "palladium(II) catalysts" should read --palladium catalysts--;

In the Specification at column 8, line 14, "L1" should read --$L_1$--;

In the Specification at column 8, line 21, "L-1-Lg" should read --$L_1$-$L_8$--;

In the Specification at column 8, line 28, "IrCl3.3H20" should read --$IRCl_3.3H_2O$--, and change "L1-Lg" to --$L_1$-$L_8$--;

In the Specification at column 8, line 36, "L1-Lg" should read --$L_1$-$L_8$--;

In the Specification at column 9, line 53, "N,N'-dicarbazole-4,4'-biphenyl" should read --*N,N'*-dicarbazole-4,4'-biphenyl--;

In the Specification at column 10, line 37, "TPBIlLiF1A1" should read --TPBI/Li/Al--;

In the Specification at column 10, line 41, "L1-Lg" should read --$L_1$-$L_8$--;

In the Specification at column 10, line 63, "M+" should read --$M^+$--;

In the Specification at column 10, line 64, "J=54 Hz" should read --J=5.4 Hz--;

In the Specification at column 12, line 2, "[Ir($L_1$)2Cl]$_2$" should read --[Ir($L_1$)$_2$Cl]$_2$-- and "Na$_2$C0$_3$" should read --$Na_2CO_3$--;

In the Specification at column 12, line 11, "M+" should read --$M^+$--, "1H NMR" should read --$^1$H NMR-- and "CDCl3" should read --$CDCl_3$--;

In the Specification at column 12, line 12, "H$_z$" should read --Hz--;

In the Specification at column 12, line 16, "CDCl3" should read --$CDCl_3$--;

In the Specification at column 15, line 22, "$\lambda_{am}$" should read --$\lambda_{em}$--;

In the Specification at column 16, line 36, "C^ N" should read --C^N--;

In the Specification at column 16, line 46, "-52 eV" should read -- -5.2 eV--;

In the Specification at column 18, line 6, "I cd/m$^2$" should read --1 cd/m$^2$--;

In the Specification at column 18, line 9, "-5 V" should read --~5 V--;

In the Specification at column 18, line 10, "-572 nm" should read --~572 nm--;

In the Specification at column 18, line 11, "0045" should read --0.45--;

In the Specification at column 18, line 16, "cd/m2" should read --cd/m$^2$--;

In the Specification at column 18, line 17, "cd/m2" should read --cd/m$^2$--;

CERTIFICATE OF CORRECTION (continued)
U.S. Pat. No. 7,652,136 B2

In the Specification at column 18, line 21, "based on I" should read --based on 1--;

In the Specification at column 18, line 47, "behavior of I (Tg)" should read --behavior of 1 ($T_g$)--;

In the Specification at column 18, line 51, "(next)" should read --$\eta_{ext}$--;

In the Specification at column 18, line 52, "(ηL)" should read --($\eta_L$)--;

In the Specification at column 18, line 53, "(ηp)" should read --($\eta_p$)--, "Im/W" should read --lm/W--, and "mA/cm2" should read --mA/cm$^2$--;

In the Specification at column 18, line 55, "(ηext)" should read --($\eta_{ext}$)--, "(ηL)" should read --($\eta_L$)--, "(ηp)" should read --($\eta_p$)--; and "Im/W" should read --lm/W--;

In the Specification at column 18, line 56, "(ηext)" should read "($\eta_{ext}$)", "(ηL)" should read --($\eta_L$)--, "(ηp)" should read --($\eta_p$)--, and "Im/W" should read --lm/W--;

In the Specification at column 18, line 57, "ηext, ηL, ηp" should read --$\eta_{ext}$, $\eta_L$, $\eta_p$--;

In the Specification at column 18, line 59, "Im/W" should read --lm/W--;

In the Specification, at column 18, line 61, "(ηext)" should read --($\eta_{ext}$)--;

In the Specification, at column 18, line 64, "(ηext)" should read --($\eta_{ext}$)--;

In the Specification at column 19, line 15, "15600 cd/m2" should read --15,600 cd/m$^2$--;

In the Specification at column, 19, line 16, "(ηext)" should read --($\eta_{ext}$)--, "(ηL)" should read --($\eta_L$)--, "(ηp)" should read --($\eta_p$)--, and "Im/W" should read --lm/W--;

In the Specification at column 19, line 23, "(ηext)" should read --($\eta_{ext}$)--, "(ηL)" should read --($\eta_L$)--, "(ηp)" should read --($\eta_p$)--, and "Im/W" should read --lm/W--;

In the Specification at column 19, line 24, "(ηext)" should read --($\eta_{ext}$)--, "(ηL)" should read --($\eta_L$)--, "(ηp)" should read --($\eta_p$)--, and "Im/W" should read --lm/W--;

In the Specification at column 19, line 38, "(mCP=N,N'-dicarbazolyl-3," should read -- (mCP=*N,N'*-dicarbazolyl-3--;

In the Specification at column 26, line 67, "Fir-Pic" should read --FIr-Pic--.